(12) United States Patent
Madwar et al.

(10) Patent No.: US 12,303,501 B2
(45) Date of Patent: *May 20, 2025

(54) LIPOPHILIC ACTIVE ORAL FILM FORMULATION AND METHOD OF MAKING THE SAME

(71) Applicant: INTELGENX CORP., St-Laurent (CA)

(72) Inventors: Carolin Madwar, Montréal (CA); Nadine Paiement, St-Laurent (CA); Rodolphe Obeid, Pierrefonds (CA); Justin W. Conway, Carignan (CA); Erick Gonzalez-Labrada, Cote Saint-Luc (CA)

( * ) Notice: Subject to any disclaimer, the term of this patent is extended or adjusted under 35 U.S.C. 154(b) by 851 days.

This patent is subject to a terminal disclaimer.

(21) Appl. No.: 17/291,582

(22) PCT Filed: Nov. 4, 2019

(86) PCT No.: PCT/CA2019/051564
§ 371 (c)(1),
(2) Date: May 5, 2021

(87) PCT Pub. No.: WO2020/093146
PCT Pub. Date: May 14, 2020

(65) Prior Publication Data
US 2021/0393611 A1   Dec. 23, 2021

Related U.S. Application Data

(63) Continuation-in-part of application No. 16/383,813, filed on Apr. 15, 2019, now Pat. No. 11,602,504.

(60) Provisional application No. 62/755,878, filed on Nov. 5, 2018.

(51) Int. Cl.
| | | |
|---|---|---|
| A61K 31/47 | (2006.01) | |
| A61K 9/00 | (2006.01) | |
| A61K 9/107 | (2006.01) | |
| A61K 31/352 | (2006.01) | |
| A61K 47/44 | (2017.01) | |

(52) U.S. Cl.
CPC ............. *A61K 31/47* (2013.01); *A61K 9/006* (2013.01); *A61K 9/107* (2013.01); *A61K 31/352* (2013.01); *A61K 47/44* (2013.01)

(58) Field of Classification Search
CPC ........ A61K 31/47; A61K 9/006; A61K 9/107; A61K 31/352; A61K 47/44
See application file for complete search history.

(56) References Cited

U.S. PATENT DOCUMENTS

| | | | |
|---|---|---|---|
| 4,695,463 A | 9/1987 | Yang et al. | |
| 6,660,292 B2 | 12/2003 | Zerbe et al. | |
| 7,132,113 B2 | 11/2006 | Zerbe et al. | |
| 7,674,479 B2 | 3/2010 | Zerbe et al. | |
| 8,642,080 B2 | 2/2014 | Bender et al. | |
| 8,691,272 B2 | 4/2014 | Zerbe et al. | |
| 8,703,191 B2 | 4/2014 | Zerbe et al. | |
| 8,735,374 B2 | 5/2014 | Zerbe et al. | |
| 9,301,948 B2 | 4/2016 | Zerbe et al. | |
| 9,668,970 B2 | 6/2017 | Obeid et al. | |
| 9,717,682 B2 | 8/2017 | Zerbe et al. | |
| 9,833,461 B2 | 12/2017 | Modi | |
| 9,949,934 B1 | 4/2018 | Zerbe et al. | |
| 10,272,038 B2 | 4/2019 | Obeid et al. | |
| 10,406,186 B2 | 9/2019 | Finley et al. | |
| 10,603,301 B2 | 3/2020 | Sinai et al. | |
| 10,610,528 B2 | 4/2020 | Zerbe et al. | |
| 10,722,476 B2 | 7/2020 | Zerbe et al. | |
| 10,828,254 B2 | 11/2020 | Paiement et al. | |
| 10,940,173 B2 | 3/2021 | Finley et al. | |
| 11,033,493 B2 | 6/2021 | Obeid et al. | |
| 11,471,406 B2 | 10/2022 | Paiement et al. | |
| 11,602,504 B2 * | 3/2023 | Madwar | A61K 36/484 |
| 11,648,212 B2 | 5/2023 | Bilal et al. | |

(Continued)

FOREIGN PATENT DOCUMENTS

| | | |
|---|---|---|
| CA | 2489106 | 12/2003 |
| CA | 2910206 | 12/2015 |

(Continued)

OTHER PUBLICATIONS

Balakrishnan, P., et al. Enhanced oral bioavailability of Coenzyme Q10 by self-emulsifying drug delivery systems. International journal of pharmaceutics, (2009). 374(1-2), 66-72. (Year: 2009).*
Hallucinogens: LSD, Peyote, Psilocybin, and PCP. National Institute on Drug Abuse (2008).
Morepen Active Ingredients, retrieved from the Internet at http://morepen.com/api-product-information.htm on Dec. 31, 2019. (Year 2019).
Baliga, S. et al. "Salivary pH: A diagnostic biomarker". J Indian Soc Periodontol, 17(4) :461-465 (Jul.-Aug. 2013).
Khatoon, N. et al. "Formulation and evaluation of oral fast dissolving films of montelukast sodium". International Journal of Pharmaceutical Sciences and Research, 5: 1780-1787 (May 2014).
The Dow Chemical Company, "Hydroxyethyl Cellulose" (Mar. 2002).

(Continued)

*Primary Examiner* — Matthew P Coughlin
*Assistant Examiner* — Quincy McKoy
(74) *Attorney, Agent, or Firm* — Anglehart et al.

(57) ABSTRACT

Disclosed is a description and methods for formulating oral films containing lipophilic active ingredient(s), more particularly lipophilic active having a positive log P. The method involves dispersing the lipophilic active(s) in a carrier oil and uniformly distributing them as emulsified oil droplets into a polymer matrix. The methods reported here produce oral films containing a stable emulsion with up to 40% oil phase. The oil phase consists of the carrier oil and lipophilic active(s). This offers the possibility to enhance the amount of lipophilic actives to be included in the film formulation while preserving the film characteristics. The resulting oral films offer a standardized dosage form for lipophilic actives as well as easier and more convenient administration, transportation, handling, and storage.

20 Claims, 4 Drawing Sheets

(56) References Cited

U.S. PATENT DOCUMENTS

| | | |
|---|---|---|
| 2004/0131661 A1* | 7/2004 | Auffret .................. A61K 8/733 424/443 |
| 2007/0053939 A1 | 3/2007 | Yokoyama |
| 2007/0190139 A1 | 8/2007 | Zerbe et al. |
| 2009/0214640 A1 | 8/2009 | Szabo et al. |
| 2011/0136815 A1 | 6/2011 | Zerbe et al. |
| 2011/0263606 A1 | 10/2011 | Zerbe et al. |
| 2012/0141585 A1* | 6/2012 | Coulter .................. A61P 37/02 424/464 |
| 2014/0065217 A1 | 3/2014 | Zerbe et al. |
| 2014/0155483 A1 | 6/2014 | Li et al. |
| 2015/0265720 A1 | 9/2015 | Levine et al. |
| 2016/0015683 A1 | 1/2016 | McCarty |
| 2016/0051510 A1* | 2/2016 | Allen ...................... A61K 9/006 424/443 |
| 2016/0074396 A1 | 3/2016 | Jeon |
| 2016/0220480 A1 | 8/2016 | Bilal et al. |
| 2016/0228385 A1 | 8/2016 | Sievers et al. |
| 2016/0243036 A1 | 8/2016 | Paiement et al. |
| 2016/0324773 A1 | 11/2016 | Paiement et al. |
| 2016/0346339 A1 | 12/2016 | Finley et al. |
| 2017/0216220 A1 | 8/2017 | Bilal et al. |
| 2017/0246120 A9 | 8/2017 | Stepovich |
| 2017/0252300 A1 | 9/2017 | Modi |
| 2017/0258710 A1 | 9/2017 | Conway et al. |
| 2017/0290807 A1 | 10/2017 | Mundada |
| 2017/0290870 A1* | 10/2017 | Schaneville .......... A61K 47/26 |
| 2017/0304319 A1 | 10/2017 | Westrin |
| 2017/0333387 A1 | 11/2017 | Sarne |
| 2018/0042890 A1 | 2/2018 | Sinai et al. |
| 2018/0078549 A1 | 3/2018 | Zerbe et al. |
| 2018/0110724 A1 | 4/2018 | Zerbe et al. |
| 2018/0250240 A1 | 9/2018 | Paiement et al. |
| 2018/0289665 A1 | 10/2018 | Turner et al. |
| 2018/0303791 A1 | 10/2018 | Sinai et al. |
| 2019/0060381 A1 | 2/2019 | Ballan et al. |
| 2019/0133925 A1 | 5/2019 | Paiement et al. |
| 2019/0209459 A1 | 7/2019 | Obeid et al. |
| 2019/0231685 A1 | 8/2019 | Paiement et al. |
| 2019/0247505 A1 | 8/2019 | Paiement et al. |
| 2019/0290595 A1 | 9/2019 | Zerbe et al. |
| 2019/0314293 A1 | 10/2019 | Bilal et al. |
| 2019/0314326 A1 | 10/2019 | Garti et al. |
| 2020/0054701 A1 | 2/2020 | Finley et al. |
| 2020/0093786 A1 | 3/2020 | Sinai et al. |
| 2020/0138730 A1 | 5/2020 | Madwar et al. |
| 2020/0138885 A1* | 5/2020 | Paiement .............. A61K 47/44 |
| 2020/0188348 A1 | 6/2020 | Sinai et al. |
| 2020/0215063 A1 | 7/2020 | Zerbe et al. |
| 2020/0268817 A1 | 8/2020 | Ballan et al. |
| 2021/0015738 A1 | 1/2021 | LaRosa |
| 2022/0008381 A1 | 1/2022 | Garti et al. |
| 2022/0031781 A1 | 2/2022 | Finley et al. |
| 2022/0362164 A1 | 11/2022 | Paiement et al. |
| 2022/0395452 A1 | 12/2022 | Paiement et al. |
| 2022/0409584 A1 | 12/2022 | Bilal et al. |
| 2023/0047314 A1 | 2/2023 | Paiement et al. |
| 2023/0201130 A1* | 6/2023 | Madwar .............. A61K 31/352 514/311 |
| 2023/0225965 A1 | 7/2023 | Tir et al. |
| 2023/0248660 A1 | 8/2023 | Bilal et al. |

FOREIGN PATENT DOCUMENTS

| | | | |
|---|---|---|---|
| CA | 2922959 | | 6/2016 |
| CA | 3020798 | | 10/2017 |
| CA | 2998218 | | 4/2018 |
| CA | 3044248 | | 5/2018 |
| CA | 3056944 | | 10/2018 |
| CA | 3017526 | A1 | 3/2020 |
| CN | 106176685 | A | 12/2016 |
| WO | 2008038155 | A2 | 4/2008 |
| WO | 2012121461 | A1 | 9/2012 |
| WO | 2013107810 | A1 | 7/2013 |
| WO | 2016134454 | A1 | 9/2016 |
| WO | WO-2018176149 | A1 * | 10/2018 .............. A61K 31/47 |
| WO | 2018205017 | A1 | 11/2018 |
| WO | 2020051709 | A1 | 3/2020 |
| WO | 2022165607 | A1 | 8/2022 |
| WO | 2022170442 | A1 | 8/2022 |

OTHER PUBLICATIONS

López-Olaondo et al. "Combination of ondansetron and dexamethasone in the prophylaxis of postoperative nausea and vomiting". British Journal of Anesthesia (1996), 76, 835-840.

Bala et al., "Orally dissolving strips: A new approach to oral drug delivery system", Int. Journal Investig. Apr.-Jun. 2013; 3(2): 67-76.

Hughes, L. "Ion exchange resinates—the technology behind the mystery" 2005, Pharmaceutical Technology Europe, 17(4), 38-42.

Carrier oil and dosing, 2016 (Year: 2016). (The year of publication is sufficiently earlier than the effective U.S. filing date so that the particular month of publication is not an issue).

Eleftheriadis, Georgios K. et al. Unidirectional drug release from 3D printed mucoadhesive buccal films using FDM technology: In vitro and ex vivo evaluation. European Journal of Pharmaceutics and Biopharmaceutics 144 (2019) 180-192.

Vieira, E. et al., Evaluation of Brewer's spent yeast to produce flavor enhancer nucleotides: influence of serial repitching. Aug. 20, 2013, Journal of Agricultural and Food Chemistry, vol. 61, 8724-8729.

English Translation of WO2012121461A1, published Sep. 13, 2012. Machine Translation.

Vishvakarma, "Design and development of montelukast sodium fast dissolving films for better therapeutic efficacy", Journal of the Chilean Chemical Society, 63(2), pp. 3988-3993, Jun. 1, 2018 (Jun. 1, 2018).

* cited by examiner

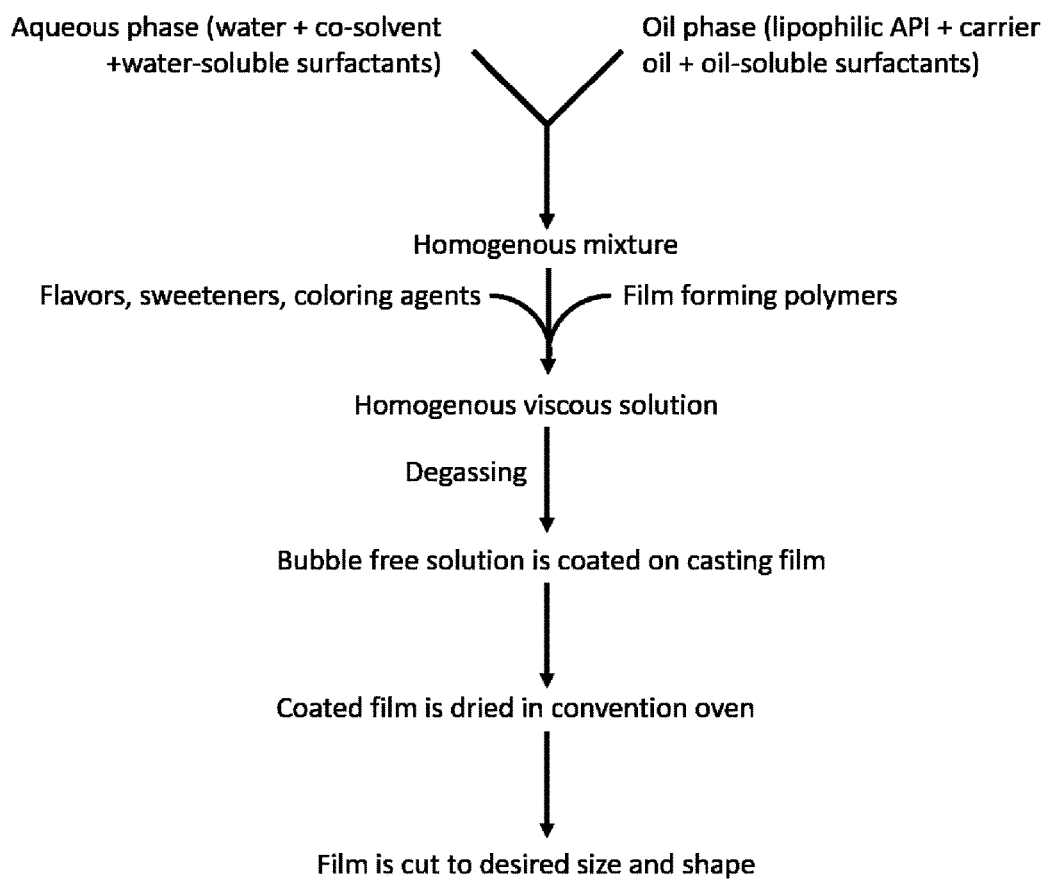
Figure 1a: Methods for preparing OFs containing lipophilic active dispersed in an oil-in-water emulsion

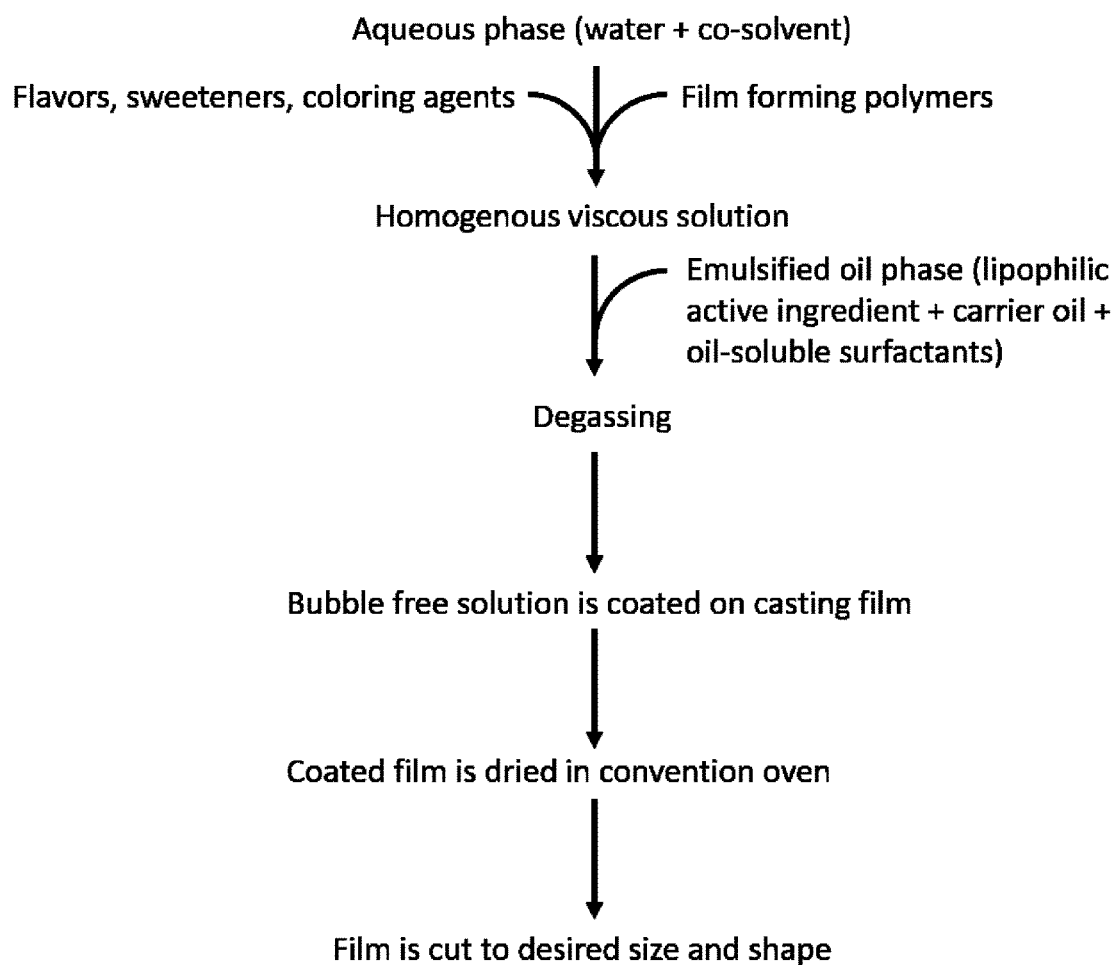
Figure 1b: Methods for preparing OFs containing lipophilic active dispersed in an oil-in-water emulsion

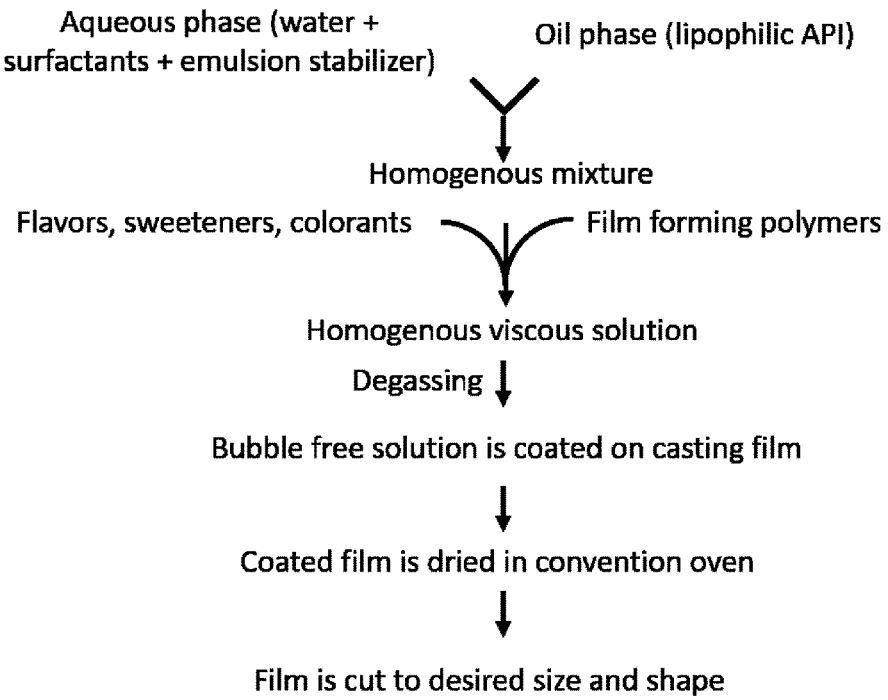
Figure 1c: Methods for preparing OFs containing lipophilic active dispersed in an oil-in-water emulsion
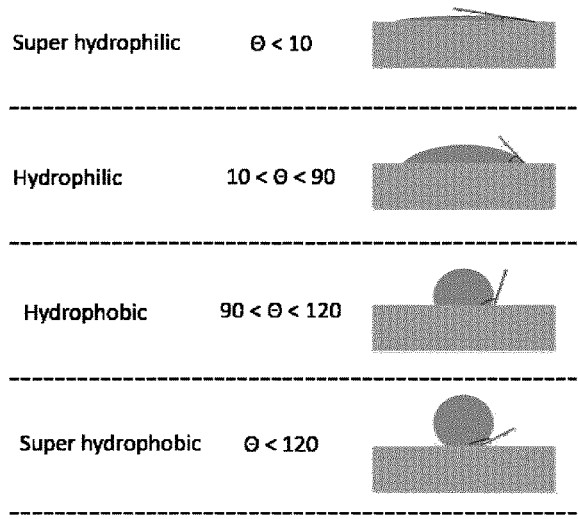
Figure 2: Classification of surface wettability using contact angle measurements

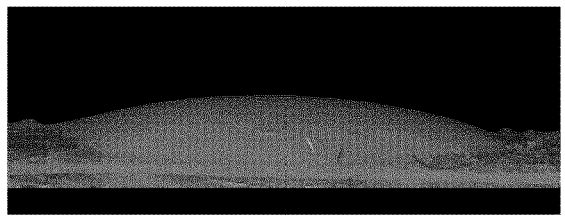 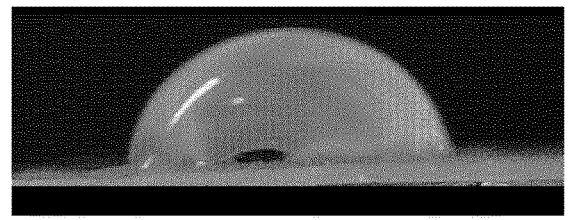
ODF with hydrophilic surface      ODF with hydrophobic surface
Figure 3: OFs with different surface wettability, illustrated in water droplet shape and contact angle measurement

LIPOPHILIC ACTIVE ORAL FILM FORMULATION AND METHOD OF MAKING THE SAME

CROSS-REFERENCE TO RELATED APPLICATIONS

This application is a 35 USC 371 national stage entry of PCT/CA2019/051564 filed on Nov. 4, 2019 that is a continuation-in-part of U.S. application Ser. No. 16/383,813, filed on Apr. 15, 2019. The present application also claims priority to U.S. Provisional Application No. 62/755,878, filed on Nov. 5, 2018. These documents are hereby incorporated by reference in their entirety.

FIELD OF THE DISCLOSURE

This disclosure concerns oral films, formulation for oral films containing lipophilic or amphiphilic active ingredients, more particularly lipophilic cannabinoids and methods of making oral films containing lipophilic actives.

BACKGROUND OF THE DISCLOSURE

The world is filled with a wide variability of biologically active molecules which are one day or another the subject of an attempt to formulate in some sort of readily available pharmaceutical product. Lipophilic actives are known to cause concern with regards to their stability in a desirably bioavailable pharmaceutical product.

The *Cannabis* plant has a long history of medicinal use, with promising clinical applications in managing symptoms associated with cancer, acquired immune deficiency syndrome (AIDS), anxiety, depression, post-traumatic stress disorder, and more. The *Cannabis* plant contains a variety of lipophilic actives such as Δ9-Tetrahydrocannabinol (THC). THC is a primary active ingredient of *Cannabis* and is responsible for many pharmacological effects of the plant. To date, the THC clinical applications approved by the Food and Drug Administration (FDA) are for the control of anorexia associated with weight loss in patients with AIDS, and nausea and vomiting associated with cancer chemotherapy in patients who have failed to respond adequately to conventional antiemetic treatments.

In addition to THC, several less potent metabolites and related compounds are found in the *Cannabis* plant, including the also psychoactive Δ8-THC and cannabinol (CBN). Another major lipophilic compound is cannabidiol (CBD), which has antagonistic effects to THC and is a sedative compound. In the United States, the CBD drug has been approved by the FDA for treatment of epilepsy disorders. Preliminary research on other possible therapeutic uses for CBD include several neurological disorders.

Leukotriene receptor antagonists, such as montelukast, zafirlukast, and pranlukast, and their various salts are also lipophilic active characterized with high log P values. Some leukotriene receptor antagonists have been successfully formulated in a tablet form, and commercialized under such dosage form, yet tablet dosage forms are known to yield poorer or lower bioavailability when compared with other dosage form. Other forms such as oral film dosage form present additional challenges from a formulation standpoint. Stability and solubility often result in oral dosage form being highly variable hence discarded or abandoned.

WO2018/176149 A1 discloses that montelukast solubility is greatly affected by the pH thereby creating important problems when aiming at formulating montelukast in an aqueous formulation. Also taught in WO2018/176149 is the need to stabilize montelukast using anti-oxidants such as EDTA and BHT which themselves affect pH and the fragile equilibrium required to maintain montelukast in a solubilized form within the aqueous oral film formulation. Montelukast solubility is thus highly dependent on pH in aqueous environment. WO2018/176149 also disclosed that solubilized montelukast increased bioavailability while requiring antioxidants to increase stability. However, antioxidants lower pH thereby affecting the form of montelukast within the blend, thus conversely hindering bioavailability, there is thus a need for suitable solution to mitigate the shortcoming of current teachings concerning montelukast formulations.

There is also a need for a lipophilic oral dosage form that mitigate the shortcomings of know lipophilic or amphiphilic active formulations.

SUMMARY OF THE DISCLOSURE

Disclosed is an oral film dosage form for lipophilic actives having low solubility in water.

According to some aspects of the disclosure, the film layer can be configured for oral transmucosal and oral delivery of the active agent(s).

According to some aspects of the disclosure, an oral film dosage form for human or animal administration comprises an oil in water emulsion based continuously cast film layer, which comprises a carrier oil, a safe and effective amount of a surfactant-like amphiphilic pharmaceutical active and a water soluble film forming polymer, the combined quantity of carrier oil and amphiphilic pharmaceutical active is more than about 10% (wt/wt) of the oral film dosage form. According to one aspect, the amphiphilic pharmaceutical active is an amphiphilic leukotriene receptor antagonist, such as Montelukast.

According to some aspects of the disclosure, the disclosed oral film dosage form for human or animal administration comprises a film layer which comprises a safe and effective amount of a lipophilic pharmaceutical active, a carrier oil and a water soluble film forming polymer. According to some aspect of the disclosure, the film containing pharmaceutical lipophilic active has a surface pH equal or lower than 7 and not less. According to other aspects of the disclosure, the lipophilic containing active film has a surface pH equal or lower than 6.5. The oral film dosage form has a combined quantity of carrier oil and lipophilic active that is more than about 5% (wt/wt), more than about 15% (wt/wt), more than about 25% (wt/wt), more than about 30% (wt/wt), more than about 35% (wt/wt), more than about 40% (wt/wt) of the oral film dosage form. The film may further comprise one or more viscosity modifier(s).

According to some aspects of the disclosure, the disclosed oral film dosage form has a film layer which retains at least 95% of the oil and lipophilic active within its polymeric matrix.

According to some aspects of the disclosure, the disclosed oral film dosage form has an emulsion based continuously cast layer having a contact angle of less than 90 degrees, less than 80 degrees, less than 70 degrees, less than 60 degrees.

According to some aspect of the disclosure, the lipophilic active is a cannabinoid such as THC or CBD and the carrier oil is MTC oil.

According to some aspect of the disclosure, the lipophilic active and the carrier oil are in the form of a *Cannabis* oil extract containing THC and CBD along with other biologically active compounds such as omega-3 fatty acids, vitamins, terpenes, flavonoids and other phytocannabinoids, such as cannabichromene (CBC), cannabigerol (CBG), cannabinol (CBN) and cannabidivarian (CBCV).

According to some aspect of the disclosure, the lipophilic active and the carrier oil are in the form of a *Cannabis* full spectrum oil extract.

According to some aspect of the disclosure, the lipophilic active and the carrier oil are in the form of a *Cannabis* distillate oil extract.

According to some aspect of the disclosure, the oral film dosage form further comprises pectin in the film layer comprising the lipophilic active or in a one or more protective layers joined to the film layer comprising the lipophilic active, the pectin being present in an amount effective to provide targeted enteric delivery of the lipophilic active to the colon or large intestine upon administration.

According to some aspects of the disclosure, the disclosed oral is a multilayer oral film dosage form comprising a core film layer comprising a safe and effective amount of a lipophilic active, a carrier oil, and a water soluble film forming polymer; and two protective layers, each of which is joined to one of opposite sides of the core film layer, the protective layers each comprising a basifying agent or base buffering component that maintains a basic pH environment when the dosage form is orally administered. According to some aspect of the disclosure, the combined quantity of carrier oil and lipophilic active is more than about 40% (wt/wt) of the oral film dosage form.

According to some aspects of the disclosure, it is disclosed a method of treating a neurodegenerative disease, comprising orally administering to a subject in need of treatment a film dosage form comprising a film layer that comprises a carrier oil, a safe and effective amount of an amphiphilic pharmaceutical active, a water soluble film forming polymer wherein the amphiphilic pharmaceutical active exhibit surfactant properties, wherein the combined quantity of carrier oil and amphiphilic pharmaceutical active is more than about 20% (wt/wt) of the oral film dosage form.

According to some aspects of the disclosure, the disclosed oral film formulation disclosed herein is suitable for lipophilic cannabinoids.

According to some aspect of the disclosure, the oral film dosage form comprises either synthetic cannabinoid such as THC or cannabinoid such as THC extracted from the *Cannabis* plant in combination or not with other cannabinoid like CBD.

According to some aspect of the disclosure, *Cannabis* oil is used to introduce cannabinoids to the film formulation.

Also disclosed is a method to produce oral films containing stable oil-in-water emulsions, in which lipophilic actives are solubilized in the oil phase of an emulsion.

The methods disclosed herein produces oral films containing up to 40% (wt/wt) of oil phase.

In other embodiments, the oral films contain up to 40% (wt/wt) of the oil phase combined with the lipophilic active(s). This enhances the amount of lipophilic actives included in the film formulation while preserving the film characteristics.

The methods disclosed herein require the use of surfactant(s) and/or other emulsifier(s) in amounts no more than 50% of the oil phase, preferably no more than 20% of the oil phase, and more preferably no more than 10% of the oil phase determined by weight of the component.

The oral films disclosed herein preferably contain at least 40% (wt/wt) film-forming polymers.

The formulation disclosed herein allows manufacture of oral films containing up to 20% (wt/wt) of lipophilic active(s).

BRIEF DESCRIPTION OF THE FIGURES

FIGS. 1*a* and 1*b* illustrate methods for preparing water-based oral films (OFs) containing a lipophilic active(s) diluted/dissolved in a carrier oil. FIG. 1*c* illustrates the process involves combining an oil-in-water emulsion with film-forming polymers then casting and drying.

FIG. 2 illustrates measurement of surface wettability/hydrophobicity using contact angle (θ).

FIG. 3 illustrates contact angle measurement of OFs having different surface wettability/hydrophobicity.

DETAILED DESCRIPTION OF ILLUSTRATIVE EMBODIMENTS

The terms "oral dissolving film," "oral dissolvable film", "oral disintegrating film", OSF, "oral soluble film", "ODF", oral chewable film, "OCF", "oral thin film", "OTF," "oral drug strip" or "oral strip" refer to a product used to administer a predetermined amount of active ingredient(s) via oral administration such as oral transmucosal absorption, sublingual delivery or buccal delivery and will be referred to throughout as oral film "OF".

The term "OCF" refers to a type of oral film that is orally administered and designed to be chewed by the subject or patient.

The term "film" refers to a type of dosage form that is distinctly different from pills, tablets, caplets, and capsules, and in which the dosage form is a thin strip of material. Such films are typically rapidly disintegrating or rapidly dissolving, but can also exhibit longer disintegration time when required. The films are generally sufficiently flexible to allow bending or even folding without breaking. The films typically have length and width dimensions on the order of 5 to 35 mm, although larger or smaller dimensions are possible and may be desirable in particular circumstances, and a thickness on the order of 5 to 300 µm, although larger or smaller thicknesses are possible and may be desirable in certain circumstances.

The term "active(s)" or "active agent(s)" refers mainly to active pharmaceutical ingredients (APIs), but may also refer generally to any agent(s) that chemically interacts with the subject to which it is administered to cause a biological change, such as, but not limited to, eliminating symptoms of disease or regulating biological functions.

The term "lipophilic" refers to good oil solubility and/or poor aqueous solubility of a substance. In the present disclosure, for example, the aqueous solubility of a lipophilic active at 37° C. is not more than 10 mg/L, preferably not more than 1 mg/L, more preferably not more than 0.5 mg/L.

Examples of lipophilic actives or lipophilic APIs with low aqueous solubility are: acitretin, albendazole, albuterol, aminoglutethimide, amiodarone, amlodipine, amphetamine, amphotericin B, atorvastatin, atovaquone, azithromycin, baclofen, beclomethasone, 6rabic6in6, benzonatate, betamethasone, bicalutanide, budesonide, bupropion, busulfan, butenafine, calcifediol, calcipotriene, calcitriol, camptothecin, candesartan, capsaicin, cannabidiol (CBD), cannabinol (CBN), cannabigerol (CBG), cannabichromene (CBC), cannabichromevarin (CBCV), cannabidivarin (CBDV), cannabigerol monomethyl ether (CBGM), cannabigerovarin (CBGV), cannabielsoin (CBE), cannabicyclol (CBL), cannabivarin (CBV), cannabicitran (CBT), 6rabic6in6o16, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nisoldipine, nilutanide, nitrofurantoin, nizatidine, omeprazole, oprevelkin, oestradiol, oxaprozin, paclitaxel, pantoprazole, paracalcitol, paroxetine, pentazocine, pioglitazone, pizofetin, pravastatin, prednisolone, probucol, progesterone, pseudoephedrine, pyridostigmine, rabeprazole, raloxifene, repaglinide, rifabutine, rifapentine, rimexolone, ritanovir, rizatriptan, rofecoxib, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, THC, tetrahydrocannabivarin (THCV), tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, Vitamin A, Vitamin D, Vitamin E, Vitamin K, zafirlukast, zileuton, zolmitriptan, zolpidem, and zopiclone. Salts, isomers and derivatives of the above-listed hydrophobic APIs may also be used, as well as mixtures thereof.

In accordance with certain aspects of this disclosure, methods of administration and devices for the improved delivery of lipophilic or amphiphilic leukotriene inhibitors are provided. This method and device involve an oral dosage form designed to deliver leukotriene inhibitors such as Montelukast, to the mouth and stomach.

In accordance with certain aspects of this disclosure, methods for treating neurodegenerative diseases and/or other conditions that are at least partially induced by leukotrienes are provided. These methods include enteral delivery or a combination of transmucosal, sublingual or both transmucosal and sublingual, along with enteral delivery of Montelukast. The Montelukast is incorporated into a film layer in an amount that is safe and effective to reduce leukotriene induced neuroinflammation in patients.

Neurodegenerative diseases that can be treated in accordance with this disclosure include, but are not limited to, loss of memory function (long term or short term), dementia, apathy, depression, fatigue (acute or chronic), cognitive losses, loss of focus, loss of libido, and disorientation. Specific disease conditions that can be treated with the disclosed methods include Huntington's disease, Parkinson's disease and Alzheimer's disease. Such treatments can also be effective for treating neurological diseases, neurodegenerative diseases, neuroinflammatory disorders, traumatic or posttraumatic disorders, vascular or more precisely, neurovascular disorders, hypoxic disorders, and postinfectious central nervous system disorders. The term "neurodegenerative disease" or "neurological disease" or "neuroinflammatory disorder" refers to any disease, disorder, or condition affecting the central or peripheral nervous system, including ADHD, AIDS-neurological complications, absence of the Septum Pellucidum, acquired epileptiform aphasia, acute disseminated encephalomyelitis, adrenoleukodystrophy, agenesis of the Corpus Callosum, agnosia, Aicardi Syndrome, Alexander Disease, Alpers' Disease, alternating hemiplegia, Alzheimer's Disease, amyotrophic lateral sclerosis (ALS), anencephaly, aneurysm, Angelman Syndrome, angiomatosis, anoxia, aphasia, apraxia, arachnoid cysts, arachnoiditis, Arnold-Chiari Malformation, arteriovenous malformation, aspartame, Asperger Syndrome, ataxia telangiectasia, ataxia, attention deficit-hyperactivity disorder, autism, autonomic dysfunction, back pain, Barth Syndrome, Batten Disease, Behcet's Disease, Bell's Palsy, benign essential blepharospasm, benign focal amyotrophy, benign intracranial hypertension, Bernhardt-Roth Syndrome, Binswanger's Disease, blepharospasm, Bloch-Sulzberger Syndrome, brachial plexus birth injuries, brachial plexus injuries, Bradbury-Eggleston Syndrome, brain aneurysm, brain injury, brain and spinal tumors, Brown-Sequard Syndrome, bulbospinal muscular atrophy, Canavan Disease, Carpal Tunnel Syndrome, causalgia, cavernomas, cavernous angioma, cavernous malformation, central cervical cord syndrome, central cord syndrome, central pain syndrome, cephalic disorders, cerebellar degeneration, cerebellar hypoplasia, cerebral aneurysm, cerebral arteriosclerosis, cerebral atrophy, cerebral beriberi, cerebral gigantism, cerebral hypoxia, cerebral palsy, cerebro-oculo-facio-skeletal syndrome, Charcot-Marie-Tooth Disorder, Chiari Malformation, chorea, choreoacanthocytosis, chronic inflammatory demyelinating polyneuropathy (CIDP), chronic orthostatic intolerance, chronic pain, Cockayne Syndrome Type II, Coffin Lowry Syndrome, coma, including persistent vegetative state, complex regional pain syndrome, congenital facial diplegia, congenital myasthenia, congenital myopathy, congenital vascular cavernous malformations, corticobasal degeneration, cranial arteritis, craniosynostosis, Creutzfeldt-Jakob Disease, cumulative trauma disorders, Cushing's Syndrome, cytomegalic inclusion body disease (CIBD), cytomegalovirus infection, dancing eyes-dancing feet syndrome, Dandy-Walker Syndrome, Dawson Disease, De Morsier's Syndrome, Dejerine-Klumpke Palsy, delir in elderly, trauma-induced delir, dementia-multi-infarct, dementia-subcortical, dementia with Lewy Bodies, dermatomyositis, developmental dyspraxia, Devic's Syndrome, diabetic neuropathy, diffuse sclerosis, Dravet's Syndrome, dysautonomia, dysgraphia, dyslexia, dysphagia, dyspraxia, dystonias, early infantile epileptic encephalopathy, Empty Sella Syndrome, encephalitis lethargica, encephalitis and meningitis, encephaloceles, encephalopathy, encephalotrigeminal angiomatosis, epilepsy, Erb's Palsy, Erb-Duchenne and Dejerine-Klumpke Palsies, Fabry's Disease, Fakir's Syndrome, fainting, familial dysautonomia, familial hemangioma, familial idiopathic basal ganglia calcification, familial spastic paralysis, febrile seizures (e.g., GEFS and GEFS plus), Fisher Syndrome, Floppy Infant Syndrome, Friedreich's Ataxia, Gaucher's Disease, Gerstmann's Syndrome, Gerstmann-Straussler-Scheinker Disease, giant cell arteritis, giant cell inclusion disease, globoid cell leukodystrophy, glossopharyngeal neuralgia, Guillain-Barre Syndrome, HTLV-1 associated myelopathy, Hallervorden-Spatz Disease, head injury, headache, hemicrania continua, hemifacial spasm, hemiplegia alterans, hereditary neuropathies, hereditary spastic paraplegia, heredopathia atactica polyneuritiformis, Herpes Zoster Oticus, Herpes Zoster, Hirayama Syndrome, holoprosencephaly, Huntington's Disease, hydranencephaly, hydrocephalus-normal pressure, hydrocephalus, hydromyelia, hypercortisolism, hypersomnia, hypertonia, hypotonia, hypoxia, immune-mediated encephalomyelitis, inclusion body myositis, incontinentia pigmenti, infantile hypotonia, infantile phytanic acid storage disease, infantile refsum disease, infantile spasms, inflammatory myopathy, intestinal lipodystrophy, intracranial cysts, intracranial hypertension, Isaac's Syndrome, Joubert Syndrome, Kearns-Sayre Syndrome, Kennedy's Disease, Kinsboume syndrome, Kleine-Levin syndrome, Klippel Feil Syndrome, Klippel-Trenaunay Syndrome (KTS), Klüiver-Bucy Syndrome, Korsakoffs Amnesic Syndrome, Krabbe Disease, Kugelberg-Welander Disease, kuru, Lambert-Eaton Myasthenic Syndrome, Landau-Kleffner Syndrome, lateral femoral cutaneous nerve entrapment, lateral medullary syndrome, learning disabilities, Leigh's Disease, Lennox-Gastaut Syndrome, Lesch-Nyhan Syndrome, leukodystrophy, Levine-Critchley Syndrome, Lewy Body Dementia, lissencephaly, locked-in syndrome, Lou Gehrig's Disease, lupus-neurological sequelae, Lyme Disease-Neurological Complications, Machado-Joseph Disease, macrencephaly, megalencephaly, Melkersson-Rosenthal Syndrome, meningitis, Menkes Disease, meralgia paresthetica, metachromatic leukodystrophy, microcephaly, migraine, Miller Fisher Syndrome, mini-strokes, mitochondrial myopathies, Mobius Syndrome, monomelic amyotrophy, motor neuron diseases, Moyamoya Disease, mucolipidoses, mucopolysaccharidoses, multi-infarct dementia, multifocal motor neuropathy, multiple sclerosis (MS), multiple systems atrophy (MSA-C and MSA-P), multiple system atrophy with orthostatic hypotension, muscular dystrophy, myasthenia-congenital, myasthenia gravis, myelinoclastic diffuse sclerosis, myoclonic encephalopathy of infants, myoclonus, myopathy-congenital, myopathy-thyrotoxic, myopathy, myotonia congenita, myotonia, narcolepsy, neuroacanthocytosis, neurodegeneration with brain iron accumulation, neurofibromatosis, neuroleptic malignant syndrome, neurological complications of AIDS, neurological manifestations of Pompe Disease, neuromyelitis optica, neuromyotonia, neuronal ceroid lipofuscinosis, neuronal migration disorders, neuropathy-hereditary, neurosarcoidosis, neurotoxicity, nevus cavernosus, Niemann-Pick Disease, O'Sullivan-McLeod Syndrome, occipital neuralgia, occult spinal dysraphism sequence, Ohtahara Syndrome, olivopontocerebellar atrophy, opsoclonus myoclonus, orthostatic hypotension, Overuse Syndrome, pain-chronic, paraneoplastic syndromes, paresthesia, Parkinson's Disease, parmyotonia congenita, paroxysmal choreoathetosis, paroxysmal hemicrania, Parry-Romberg, Pelizaeus-Merzbacher Disease, Pena Shokeir II Syndrome, perineural cysts, periodic paralyses, peripheral neuropathy, periventricular leukomalacia, persistent vegetative state, pervasive developmental disorders, phytanic acid storage disease, Pick's Disease, Piriformis Syndrome, pituitary tumors, polymyositis, Pompe Disease, porencephaly, Post-Polio Syndrome, postherpetic neuralgia, postinfectious encephalomyelitis, postural hypotension, postural orthostatic tachycardia syndrome, postural tachycardia syndrome, primary lateral sclerosis, prion diseases, progressive hemifacial atrophy, progressive locomotor ataxia, progressive multifocal leukoencephalopathy, progressive sclerosing poliodystrophy, progressive supranuclear palsy, pseudotumor cerebri, pyridoxine dependent and pyridoxine responsive seizure disorders, Ramsay Hunt Syndrome Type I, Ramsay Hunt Syndrome Type II, Rasmussen's Encephalitis and other autoimmune epilepsies, reflex sympathetic dystrophy syndrome, refsum disease-infantile, refsum disease, repetitive motion disorders, repetitive stress injuries, restless legs syndrome, retrovirus-associated myelopathy, Rett Syndrome, Reye's Syndrome, Riley-Day Syndrome, SUNCT headache, sacral nerve root cysts, Saint Vitus Dance, Salivary Gland Disease, Sandhoff Disease, Schilder's Disease, schizencephaly, seizure disorders, septo-optic dysplasia, severe myoclonic epilepsy of infancy (SMEI), shaken baby syndrome, shingles, Shy-Drager Syndrome, Sjogren's Syndrome, sleep apnea, sleeping sickness, Soto's Syndrome, spasticity, spina bifida, spinal cord infarction, spinal cord injury, spinal cord tumors, spinal muscular atrophy, spinocerebellar atrophy, Steele-Richardson-Olszewski Syndrome, Stiff-Person Syndrome, striatonigral degeneration, stroke, Sturge-Weber Syndrome, subacute sclerosing panencephalitis, subcortical arteriosclerotic encephalopathy, Swallowing Disorders, Sydenham Chorea, syncope, syphilitic spinal sclerosis, syringohydromyelia, syringomyelia, systemic lupus erythematosus, Tabes *Dorsalis*, Tardive Dyskinesia, Tarlov Cysts, Tay-Sachs Disease, temporal arteritis, tethered spinal cord syndrome, Thomsen Disease, thoracic outlet syndrome, thyrotoxic myopathy, Tic Douloureux, Todd's Paralysis, Tourette Syndrome, transient ischemic attack, transmissible spongiform encephalopathies, transverse myelitis, traumatic brain injury, tremor, trigeminal neuralgia, tropical spastic paraparesis, tuberous sclerosis, vascular erectile tumor, vasculitis including temporal arteritis, Von Economo's Disease, Von Hippel-Lindau disease (VHL), Von Recklinghausen's Disease, Wallenberg's Syndrome, Werdnig-Hoffinan Disease, Wernicke-Korsakoff Syndrome, West Syndrome, Whipple's Disease, Williams Syndrome, Wilson's Disease, X-Linked Spinal and Bulbar Muscular Atrophy, and Zellweger Syndrome.

The disclosed dosage forms and methods are expected to be especially useful for treating neurodegenerative diseases and neuroinflammatory disorders selected from the group comprising or consisting of: Alzheimer's disease, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders of multiple spontaneous or genetic background, amyotrophic lateral sclerosis (ALS), spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, multiple sclerosis (MS), acute ischemic/hypoxic lesions, stroke, CNS and spinal cord trauma, head and spinal trauma, brain traumatic injuries, arteriosclerosis, atherosclerosis, microangiopathic dementia, Binswanger' disease (Leukoaraiosis), cochlear degeneration, cochlear deafness, AIDS-related dementia, fragile X-associated tremor/ataxia syndrome (FXTAS), progressive supranuclear palsy (PSP), striatonigral degeneration (SND), olivopontocerebellear degeneration (OPCD), Shy Drager syndrome (SDS), age dependant memory deficits, neurodevelopmental disorders associated with dementia, Down's Syndrome, synucleinopathies, superoxide dismutase mutations, trinucleotide repeat disorders as Huntington's Disease, trauma, hypoxia, vascular diseases, vascular inflammations, CNS-ageing. Also age dependent decrease of stem cell renewal may be addressed.

The disclosed dosage forms and methods are expected to be especially useful for treating neurodegenerative diseases and neuroinflammatory disorders selected from the group comprising or consisting of: Alzheimer's disease, Parkinson's disease, Huntington's disease, amyotrophic lateral sclerosis (ALS), hydrocephalus, CNS and spinal cord trauma such as spinal cord injury, head and spinal trauma, brain traumatic injuries, cochlear deafness, AIDS-related dementia, trinucleotide repeat disorders as Huntington's Disease, and CNS-aging.

The words "treatment", "treating" and variations thereof refer to curing, mitigating or relieving symptoms of a disease, medical condition or injury.

As used herein, a film layer that is "unbuffered" is a film layer that does not contain a weak acid or weak base that is effective to maintain pH near a chosen value upon addition of another acid or base. Stated differently, the unbuffered film layer does not contain a buffering agent, such as borates, citrates, or phosphates.

Enteral delivery refers to passing the active agent through the gastrointestinal tract, either naturally via the mouth and esophagus, or through an artificial opening (e.g., stoma) and absorbing the active agent in the intestine.

Leukotriene inhibitions include leukotriene receptor antagonists and/or leukotriene synthesis inhibitors that block 5-lipoxygenase activity. Such leukotriene inhibitors include, but are not necessarily limited to, leukotriene receptor antagonist such as Montelukast, Zafirlukast, Pranlukast, cinalukast, probilukast, iralukast and sulukast. Active agents capable of existing in various forms, such as base form, salts, esters, prodrugs, etc., are, unless otherwise indicated, encompassed by reference to the base drug. For example, the term "Montelukast" is intended to encompass all forms, including salts (e.g., Montelukast sodium), esters and prodrugs.

The term "cannabinoid" represents a group of C21 terpenophenolic compounds found uniquely in *Cannabis* plants. Cannabinoids include the psychoactive compounds 49-tetrahydrocannabinol (THC), Δ8-THC, cannabinol (CBN), 11-hydroxy Δ9-THC, anandamide, and the non-psychoactive compounds cannabidiol (CBD), cannabichromene, and (−) Δ8-THC-11-oic acid. Cannabinoids can be synthetically made or can be extracted from the *Cannabis* plant. The term cannabinoid is used herein to refer to cannabinoid that is either synthetic or extracted from the plant. It is also used to refer to a single cannabinoid or mixture of cannabinoids.

The term "*Cannabis*" is used to refer to plants of the genus *Cannabis*, including *Cannabis sativa* and *Cannabis indica*.

Montelukast as used herein is referring to both forms of Montelukast, Montelukast Sodium and the protonated form of Montelukast which both exhibit strong lipophilic characteristics with a log P of 7.8.

The term "film former polymers" refers to water-soluble or water dispersible polymers of common pharmaceutical use that conform to the required properties, including, but not limited to, film instant hydration potential, mucoadhesion and solubility over time. Examples of film forming polymers include cellulose derivatives, polyvinyl alcohol, polyvinyl pyrrolidone, polyethylene oxide, starches, polyacrylates, gums (xanthan gum, arabic gum, guar gum, etc.) and/or mixtures thereof. Film forming polymers may be used in combinations chosen based on the desired characteristics of the delivery form (e.g., rapid disintegration, higher mucoadhesion, longer residence time, etc.). Some of the film forming polymers may also act as emulsifier, bioavailability enhancer and or viscosity modifier.

The term "food-grade material" refers to material that is either safe for human consumption or it is authorized by the health authorities or at least one health authority to come into direct contact with food products. Food-grade material herein includes food-grade polymers, surfactant, emulsifiers, stabilizers, oils or any other food grade material suitable for oral film manufacturing.

The term "food safe material" means that a food-grade material is also suitable for its intended use and will not create a food-safety hazard.

According to some embodiments, OF formulations suitable for lipophilic APIs are disclosed.

According to some embodiments, the lipophilic actives (e.g., montelukast, zafirlukast, lipophilic cannabinoids, etc.) used in the water-based OF formulations disclosed herein are diluted/dissolved in an oil vehicle (i.e., a carrier oil). The term "carrier oil" is used to describe a hydrocarbon liquid substance that is typically greasy to the touch, generally formed by natural resources or the breakdown of fats, serves the purpose of diluting a lipophilic active ingredient. The term carrier oil is derived from the purpose of carrying the active ingredient into the formulation. The carrier oil provides a great practicality for high load of lipophilic, poorly water soluble APIs. The carrier oil containing the API is added to the aqueous solution/blend to produce an oil-in-water emulsion.

According to some embodiments, the amphiphilic actives (e.g., montelukast, zafirlukast, etc.) used in the water-based OF formulations disclosed herein are dissolved or partially solubilized in aqueous solution/blend with a predetermined pH. An oil carrier is then added to the API aqueous solution/blend to generate an oil-in-water emulsion.

According to some embodiment, the active is added to the carrier oil which is then added to the aqueous solution/blend to generate an oil-in-water emulsion.

According to some embodiments, the lipohilic actives used in the water-based OF formulations disclosed herein are added to an emulsified aqueous phase. The mixture is then homogenized to form a stable oil-in-water emulsion. In some embodiments, other oil vehicles (such as flavor oils) are added to this stabilized oil-in-water emulsion and further homogenized.

Lipophilic active is also understood to refer to actives with a positive log P value. The partition coefficient (P) describes the propensity of a neutral (uncharged) compound to dissolve in an immiscible biphasic system of lipid (i.e., fats, oils, organic solvents) and water. The P value measures how much the compound dissolves in the water portion versus an organic portion. The log P value is a constant defined as: log P=log 10 (Partition Coefficient), in which Partition Coefficient, P represent the concentration of compound in an organic phase/concentration of compound in an aqueous phase. A negative value for log P means the compound has a higher affinity for the aqueous phase (i.e., it is more hydrophilic). A log P of 0 represent that the compound is equally partitioned between the lipid and aqueous phases while a positive value for log P denotes a higher concentration in the lipid phase (i.e., the compound is more lipophilic). A log P of 1 means that there is a 10:1 ratio organic phase: aqueous phase.

At least some lipophilic actives such as Montelukast are known to have a solubility which is highly sensitive to changes in pH environment and resulting in a rapid precipitation of the active below pH 8. Montelukast is both a lipophilic active and an amphiphilic active. Montelukast, Zafirlukast and Pranlukast are known CysLTiR antagonist. Montelukast, Zafirlukast and Pranlukast are all amphiphilic compound with distinct lipophilic and acidic regions which explains their lipophilic character and their characterization herein as lipophilic actives.

The term "amphiphilic" refers to compounds that contain hydrophobic and hydrophilic groups, they reduce the surface tension between two immiscible liquids and the interfacial tension between a liquid and a solid and are often referred to as surfactants. They also refer to compound (such as a surfactant) consisting of molecules having a polar water-soluble group attached to a water-insoluble hydrocarbon chain.

Examples of amphiphilic actives or amphiphilic APIs are montelukast, zafirlukast, Venlafaxine, Doxepin, Cetirizine, Chloropramine, Promethazine, Cyprohepatadine, Desipramine, Carbamazepine, Quetiapine, Mirtazapine, Raclopride, Nortryptiline, Asenapine, Amoxapine, Olanzapine, betaxolol, Pirenperone, chlorpheniramine, Escitalopram, Metoprolol, Doxorubicin, Vinorelbine, Tamoxifen, Fluoxetine, Amiodaron, Chlorpromazine, Imipramine, Loxapine, Cyclobenzaprine, desloratadine, Levocetirizine, Losartan, Amphotericin B, phenothiazine and benzodiazepine tranquilizers such as chlorpromazine HCl, promazine HCl, promethazine HCl, and thioridazine HCl; analgesics such as dextropropoxyphene; antibiotics such as actinomycin D, penicillin G, streptomycin, sodium fusidate, antihistamines such as bromodiphenyl hydramine HCl, chlorcyclizine HCl, diphenhydramine HCl, diphenylpyraline HCl, thenyldiamine HCl, tripelennamine HCl; anticholinergics such as Adiphenine HC, chlorphenoxamine HCl, orphenadrine HCl, local anesthetics such as dibucaine HCl, stadacaine HCl, tetracaine HCl. Phospholipids containing agents, and cholesterol and its derivatives.

During development of the montelukast OF, it was discovered that blending montelukast in large scale aqueous solution present significant challenges due to foaming issues. Foaming, depending on its extent, often hinders large scale processes of pharmaceutical preparations at various stages of the manufacture. For instances, foaming will impact the blending of the OF formulations. Foaming is specifically an issue for OF manufacture because of the criticality of the content uniformity in the various stage of processing and ultimately in the finished coated product. Content uniformity is assessed at various stages to ensure content uniformity is maintained throughout the manufacture process. Content uniformity is thus affected by the distribution of the active within the blend. Content uniformity is related to the amount or concentration of active by volume (for a specific film size and thickness). Foaming during the blending process expands the blend volume (via creation of air or gas bubble within the blend) thereby affecting the API distribution or content uniformity within the bulk liquid. Excessive foaming will prevent the uniform mixing to be performed, hence likely leading to content uniformity issues with the blend and any subsequent steps such as coating and drying of the inadequately mixed blend. Foaming is also problematic for the finished product as the presence of bubbles weaken the physical characteristics and esthetic of the film.

Amphiphilic actives are by default lipophilic to some extent. Their hydrophobic group will give a lipophilic character to the active. Amphiphilic actives are challenging to work with especially at the large scale manufacturing because of their potential to behave as surfactant. Especially in OF manufacture, an amphiphilic active creates additional burden due to the critical issue of potentially having a foaming related content uniformity issue Montelukast foaming issues were first discovered when, during the blend manufacture, montelukast is dissolved in water first, followed by addition of the polymers and then exposure of montelukast to high mixing shear stress in presence of film forming polymers. Foaming issues are often addressed via degassing of the blend. However, in the montelukast case, it was found to be impossible to degas the blend. Foaming issues of such a magnitude were unforeseen in manufacturing and developing oral film product. None of the previously formulated product had given the rise to such extensive and stable foaming. Montelukast unexpectedly yielded foaming that was so predominant, it was affecting the blend content uniformity and final film physical characteristics.

One alternative solution to overcome this issue is to add montelukast at the end of the blending process after all ingredients including the polymers are being completely dissolved and the blend is fully degassed. However, adding montelukast at the end is not ideal at this point because viscosity of the blend is high. The higher viscosity has the potential to also impact the ease of dispersion and dissolution of montelukast within the blend. The higher the viscosity the harder it gets to adequately and timely disperse and solubilize uniformly the active within the blend.

An alternate, more desirable way to address the foaming issue is to produce an emulsion based OF where the amphiphilic active is in an oil in water emulsion, the active would locate itself most likely at the oil/aqueous interface.

According to an alternate embodiment, the emulsion is created after the polymers have already been added to the aqueous phase.

According to some embodiment, the emulsion based OF are made using high shear homogenizing to create the emulsion then the film forming polymers are added to create the final blend.

WO2018176149A1 discloses that experimental studies have revealed that montelukast is particularly susceptible to metal catalyzed degradation as well as other oxidative or photo-induced decomposition pathways when montelukast is in its solubilized state. Existing montelukast dosage forms are predominantly found as tablets, tablet variants or suspensions in which montelukast is a solid or a suspension. In these formulas antioxidants/stabilizers can be directly added as solid material or applied to the product indirectly (spray coatings, shells or film coating). There is no need to consider antioxidant/stabilizer interactions which would precipitate montelukast in a tablet dosage form, as it is already a solid. Our studies have shown that film formulas of montelukast using only BHT as an antioxidant, exhibit increased impurities after 3 months in the stability chamber (25° C./65% RH). Chelating agents were thus used to prevent the observed extent of degradation. Examples of chelating agent include but is not limited to, molecules such as disodium edetate (EDTA), tetra sodium edetate, calcium disodium edetate, pentetic acid (DTP A), citric acid (CA), DL-2,3-Dimercapto-1-propanesulfonic (DMPS), dimercaptosuccinic acid (DMSA), monoisoamyl DMSA (MiADMSA) alpha lipoic acid (ALA), glutathione, N-acetyl-cystein (NAC), vitamin C, (2)-2-amino-3-methyl-3-sulfanylbutanoic acid, dithioglycerine, N-(alpha-L-arabinofuranos-1-yl)-L-cystein or nitrilotriacetic acid (NTP). In some cases, chelators such as EDTA are offered as different salts which exhibit more alkaline pH effects on the aqueous media, however these molecules, such as tetra sodium edetate or disodium calcium edetate do not perform as well in maintaining montelukast stability in long term studies. The greater the concentration of EDTA the greater the stability of the montelukast api. However, addition of chelators in an aqueous medium in general leads to deprotonation of the chelators and consequent acidification of the aqueous blend. This is problematic as montelukast solubility is particularly sensitive to changes in the pH of the environment and rapidly precipitates at pH below 8. In fact, only a limited amount of EDTA was able to be added to a solution of montelukast before precipitation was observed.

WO2018176149A1 also emphasized that the solubility and stability of montelukast are critical parameters to consider when formulating oral films that will generate a reproducible target bioavailability and stable product. Therefore, optimal formulations of montelukast will need to balance the amount of API with EDTA in order to achieve the needed stability while maintaining a solubilized drug component. This can be achieved using several strategies: (1) balancing the ratio of EDTA to montelukast (montelukast itself is a basifying agent), (2) using base modifying excipients to compensate for increasing amounts of EDTA, and (3) application of alkaline buffering components. Yet all the solutions presented in WO2018176149A1 required montelukast to be sustained in soluble state in an aqueous environment. This environment is thus highly affected by the pH of the aqueous environment.

Embodiments of the present disclosure, present a solution to mitigate the shortcomings of the prior art in regards to the need to use pH specific aqueous environment. The disclosed solution entails the use of oil-in-water emulsion of the montelukast (but could as well apply to other amphiphilic actives). The oil in water emulsion allows montelukast to be at the interface of the oil and water emulsion system.

According to some aspects of the disclosure, the OF formulations are water based, and include an oil-in-water emulsion. The emulsion is typically made up of oil phase, water phase, and at least surfactant(s) and/or other emulsifier(s).

According to some embodiments, the OF formulation disclosed is suitable for oral, sublingual or buccal delivery of lipophilic actives including lipophilic cannabinoids. Administering lipophilic actives using the disclosed OFs improves administration convenience, mitigates dosage uncertainty, and improves patient acceptability when compared to other known lipophilic actives method of administration such as pills, tablet, smoking and some available edibles.

According to the disclosure, lipophilic actives that can be formulated into Ofs as disclosed herein include montelukast, zafirlukast, pranlukast, THC, CBD, other cannabinoid derivatives or a mixture thereof, some of which, in their pure form, are viscous oil of high lipid solubility and low aqueous solubility (i.e. for THC solubility in water 2.8 mg/mL, log P 7.29).

According to certain embodiments, the lipophilic active includes montelukast, zafirlukast, pranlukast and their salts, particularly active having a high log P value such as Montelukast Sodium.

According to certain embodiments, the OF formulations described herein uses carrier oil (one or a mixture of carrier oils) to help bring down the overall viscosity of cannabinoids, such as THC with or without other cannabinoids, thus easing handling requirement during manufacture and promoting the production of water-compatible mixtures and formulations. Cannabinoid lipophilicity, viscous nature, and chemical instability (THC is susceptible to decomposition by oxidation, heat, acid, and light) is generally an impediment to the development of commercially viable and effective formulation for human and animal administration.

CBD is another example of lipophilic cannabinoids that can be formulated into OFs as disclosed herein. Similar to THC, CBD is poorly soluble in water, but is soluble in oil due to its high lipophilicity (solubility in water 0.0126 mg/mL, log P 6.1).

According to certain embodiments, the water-based OF formulations disclosed herein are also suitable for *Cannabis* isolates (e.g., THC oil extract or CBD oil extract or THC/CBD oils) as well as full spectrum *Cannabis* extracts (i.e., combinations of cannabinoids and terpenes) or for *Cannabis* distillate. The formulations are also suitable for synthetic cannabinoids and their derivatives.

In accordance with certain aspects of this disclosure, the carrier oil can be, but not limited to, almond oil, apricot kernel oil, avocado oil, borage seed oil, *camellia* seed oil, caprylic/capric triglycerides, castor oil (or hydrogenated castor oil), coconut oil, cranberry seed oil, cocoa butter (eg, deodorized cocoa butter oil), corn oil, grapeseed oil, hazelnut oil, hemp seed oil, macadamia nut oil, olive oil, peanut oil, pecan oil, perilla oil, pine nut oil, pistachio oil, poppy seed oil, pumpkin seed oil, rice bran oil, safflower oil, sesame oil, shea butter, soybean oil, sunflower oil, walnut oil, terpenes, flavonoids or watermelon seed oil.

According to the disclosure, the carrier oil can be mixtures of mono-, di- and tri-fatty acid esters of glycerol, and mono- and di-fatty acid esters of polyethylene glycol, known as polyoxyethylated fatty acid glycerides. Polyoxyethylated fatty acid glycerides can be prepared by esterification of glycerol and polyethylene glycol with fatty acids. The polyethylene glycol used can have an average of 6 ethylene oxide units (e.g., PEG-6, also referred to as MACROGOL-6). The fatty acids that can be used include, for example, oleic acid, lauric acid and lionleic acid. A specific example of a suitable mixture of polyoxyethylated fatty acid glycerides is oleoyl polyoxy-6 glycerides (also known as oleoyl macrogol-6 glycerides and PEG-6 glyceryl oleates), which is a mixture of mono-, di- and tri-oleic acid esters of glycerol and mono- and di-oleic acid esters of polyethylene glycol (PEG-6). Oleoyl polyoxy-6 glycerides also referred to as Apricot kernel oil PEG-6 esters are commercially available as Labrafil® M 1944 CS (Gattefosse Corporation, Paramus, N.J.). Another example of a suitable mixture of polyoxyethylated fatty acid glycerides that can be used as a carrier oil in the disclosed oral film dosage forms is linoleoyl polyoxyl-6 glycerides (also known as lineoleoyl macrogol-6 glycerides and PEG-6 glyceryl linoleates), which is a mixture of mono-, di- and tri-linoleic acid esters of glycerol and mono- and di-linoleic acid esters of polyethylene glycol (PEG-6). Linoleoyl polyoxyl-6 glycerides are commercially available as Labrafil® M2125 CS (Gattefosse Corporation, Paramus, N.J.). Another example of a mixture of polyoxyethylated fatty acid glycerides that may be useful in the disclosed oral film dosage forms is lauroyl polyoxyl-6 glycerides (also known as lauroyl macrogol-6 glycerides and PEG-6 glyceryl laurates), which is a mixture of mono-, di- and tri-lauric acid esters of glycerol and mono- and di-lauric acid esters of polyethylene glycol (PEG-6). Lauroyl polyoxyl-6 glycerides are commercially available as Labrafil® M2130 CS (Gattefossé Corporation, Paramus, N.J.). Mixtures of any of the foregoing or other polyoxyethylated fatty acid glycerides may be used in the disclosed oral film dosage forms.

According to embodiments, the carrier oil can be a flavor oil, including natural essential oils, natural flavors, artificial flavors or a mixture of these. Examples of natural essential oils include almond, apple cider, vanilla, lemon, flavonoids, lime, rosemary, sage, spearmint, thyme, Wintergreen, nutmeg, orange, peppermint, eucalyptus, ginger, juniper berry, cinnamon, anise, basil, and cardamom.

According to some embodiments, the amount of carrier oil in formulations is preferable higher than the film content of the lipophilic active(s). According to one embodiment, 50% or more of the film oil content is carrier oil. The carrier oil is dissolves the lipophilic active(s) and promote its incorporation within the film matrix. The methods disclosed herein are designed for manufacturing or producing OFs containing an oil phase.

According to some embodiments, up to 40% (wt/wt) of the OF content is the oil phase, amounting of up to 40% determined by weight of oil component per layer. Dosage strength may be increased by using the multilayer film approach, by having an OF comprising a plurality of layers such as a bilayer film, a trilayer film and other type of multilayer as long as the thickness of the film is not negatively impacting the ease of administration. In other embodiments, the oil phase combined with the lipophilic active(s) makes up to 40% (wt/wt) of the OFs composition. The carrier oil used in the emulsion formulation process is a lipid, which provides a great practicality for loading lipophilic/poorly water soluble actives. The ability to load high oil content in a OF is desirable, especially if it allows incorporation of higher content of lipophilic active agent(s).

Uptake of lipophilic and amphiphilic actives in the oral cavity using OF can be surprisingly improved using a multilayer film strategy. In its simplest embodiment, a multilayer OF consists of at least two layers. The first layer which contains the API and muco-adhesive polymers to ensure adhesion and close contact with the oral mucosa. The second layer, or backing layer, serves to slow the dissolution and/or disintegration of the OF by limiting the wetting of the active layer, while at the same time reducing abrasion from the tongue and cheek. This technique, direct and favor the absorption of the lipophilic active from the active layer into the oral mucosa and underlying capillaries. This approach is favored compared to having the active layer quickly disintegrated and swallowed. This multilayer OF comprises, but is not limited to, a bilayer OF. Embodiment of the disclosed multilayer OF could potentially incorporate other multilayers OF beyond the bilayer OF described herein. Additional layers may serve to further protect the active layer in modular time scales or for other desired purposes. Furthermore, the protective layer could be composed of variable percentage (% w/w) of high molecular polymers to control the rate of disintegration and residence time in the oral cavity. Examples of high MW polymers that would be effective includes, but are not limited to pectin, carrageenan, cellulose gum, methyl cellulose, methyl ethyl cellulose, carboxy methyl cellulose, hydroxyl propyl cellulose, hydroxyl propyl methyl cellylose, hydroxyl ethyl cellulose, pullulan, polyvinylpyrrolidone, polyvinyl acetate, poly ethylene oxide.

At least some lipophilic actives such as montelukast are known to have a solubility which is highly sensitive to changes in pH environment and resulting in a rapid precipitation of the active below pH 8. The pH within the mouth typically ranges from pH 6-7.5. Therefore, oral administration of a monolayer montelukast OF typically result in saliva induced solubilization of the OF liberating the montelukast from the solidified OF matrix. Some of the liberated montelukast not absorbed directly into the oral mucosa is thus exposed to the oral lower pH environment. This lower pH environment precipitates the montelukast before being swallowed. Maintaining amorphous solubilized montelukast within the film promotes increased bioavailability. Therefore, the disclosed multilayer OF is believed to improve the montelukast OF bioavailability by mitigating impact of the local pH by hindering lower pH fluid to directly interact with the montelukast.

According to some embodiments, the multilayer OF is designed with base buffering agents or general basifying excipients such as NaOH or organic bases such as trimethylamine ("TEA"). In another embodiments of the multilayer OF, the OF comprises an active layer directly positioned against the mucosa, a middle protecting layer, and a third layer containing basifying agents or base buffering components to maintain the pH above 8. The middle protecting layer thus at least partially shield the active layer from the basifying or base buffering layer.

Although lipophilic active OF are generally designed to favor oral cavity uptake, a portion of the OF and lipophilic active will be swallowed.

According to some embodiments, OF are designed for enteric lipophilic delivery. Uptake of swallowed lipophilic active such as leukotriene receptor antagonist will be improved by employing a multilayered OF. In the enteric absorption multilayer OF, the active layer containing the lipophilic active is sandwiched between two protective layers. These outer layers desirably comprise basifying agents or base buffering components that maintain or promote a basic pH environment as the OF is orally administered, thereby increasing/maintaining pH sensitive montelukast' solubility and thus improving uptake of the pH sensitive active in the digestive track.

According to other embodiments, the multilayer OF comprises a first and second protective layer with an active layer in between the first and second protecting layers. The protective layers each comprising at least one cationic polymers or gums such as chitosan, poly-lysine or tara gum (Polycos44). The central active montelukast layer could be comprised of solubilized montelukast which carries a negative charge, therefore a cationic polymer or gum would form an electrostatic complex with the active. This complexation would serve to protect the montelukast from degradation and precipitation in the highly acidic regions of the stomach, allowing more active drug to reach the lower intestine and be absorbed in the alkaline environment. This strategy of electrostatic complexation for API charge neutralization can also be employed in the reverse context using anionic excipients and a positively charged API.

According to some embodiment, the multilayered OF comprises at least one layer that is emulsion based and at least another layer that is not emulsion based. An exemplary embodiment for this mixed system multilayered OF is an OF where a first layer is emulsion based and a second layered is buffered to maintain the active under a certain pH diffusion environment, this second buffer layer is not an emulsion based film layer. The buffer layer in this exemplary embodiment is a aqueous based buffer layer comprising a water soluble polymer with a buffering system. Understandably, this buffering layer may further comprise plasticizer, or other additive to make sure that the second layer exhibit the required physical properties.

A multilayered oral film design could also be used to create a targeted delivery system for enterally administered montelukast. In this embodiment the active layer would be sandwiched or laminated on a single side with a pectin based film layer. Pectin is well suited for colon-specific or lower intestine drug delivery as it is selectively digested by colonic microflora to release drug with minimal degradation in upper gastrointestinal tract. Therefore, a film matrix comprised of pectin and montelukast would serve to protect the montelukast from degradation and precipitation in the acidic conditions of the stomach, allowing the drug-pectin complex to reach the lower digestive track. The matrix is then degraded by site-specific locally active pectinases which release the montelukast into the favorable alkaline environment, thereby facilitating uptake/absorption. This strategy is not limited to pectin and could be used with any site-specifically degraded film forming excipient. Furthermore, this strategy can be used in combination with any of the other multilayer strategies disclosed herein.

According to certain embodiments, the multilayered film using pectin as an active stomach protecting agent could be used with other lipophilic actives which exhibit sensitivity to acid or are prone to degradation in the presence of strong acidic environment.

According to certain embodiments, the OF products are capable of accommodating a wide range of amounts of the lipophilic active ingredient. The OFs are capable of providing an accurate dosage amount (determined by the size of the film and concentration of the active in the original oil in water emulsion) regardless of whether the required dosage is high or extremely low. Therefore, depending on the type of active or pharmaceutical composition that is incorporated into the film, the active amount may be as high as about 100 mg, desirably up to about 50 mg, more desirably up to 40 mg or as low as the microgram range, or any amount there between.

The OF products and methods according to some aspect of the present disclosure are well suited for high potency, low dosage drugs. This is accomplished through the high degree of uniformity of the films and stability of the lipophilic active through the oil in water emulsion.

According to certain embodiments, the methods disclosed herein comprise the use of surfactant(s) and/or other emulsifier(s))/emulsifiers in amounts no more than 50% of the oil phase (wt/wt), preferably no more than 20% of the oil phase, and more preferably no more than 10% of the oil phase.

According to certain embodiments, the OFs disclosed herein preferably also contain at least 40% (wt/wt) film-forming polymer(s).

According to certain embodiments, the OFs disclosed herein preferably also contain at least 0.1 to 40% (wt/wt) flavoring agent(s).

According to certain embodiments, the OFs disclosed herein preferably also contain at least 0.1 to 10% (wt/wt) bitter masker(s).

According to certain embodiments, the OFs disclosed herein preferably also contain at least 0.1 to 10% (wt/wt) flavor enhancer(s).

According to certain embodiments, the OFs disclosed herein preferably also contain at least 0.1 to 20% (wt/wt) sweetener(s).

According to certain embodiments, the OFs disclosed herein preferably also contain at least 0.1 to 2% (wt/wt) salt(s).

According to certain embodiments, the OFs disclosed herein preferably also contain at least 0.1 to 10% (wt/wt) anti-oxidant(s).

According to certain embodiments, the OF products and methods according to some aspect of the present disclosure are well suited to provide acceptable overall flavor profile as well for high potency dosage drugs, low dosage drugs.

In other aspect, the overall flavor profile could be addressed in a monolayer or multilayer OF product for high potency dosage drugs or low dosage drugs.

According to certain embodiments, incorporating lipophilic active(s)/carrier oil in water-based OFs is achieved by dispersing the excipients in water. This dispersion is promoted by the use of at least 2 percent, preferable 5 and more preferably more than 10% more preferably more than 15% of surfactants and/or film former polymer with emulsifying properties in amounts no more than 50% emulsifiers. Emulsifiers are substances that reduce the surface tension at the interface of two normally immiscible phases, allowing them to mix and form an emulsion. Surfactants are one class of the oil phase (wt/wt), preferably no more than 20% of the oil phase, and more preferably no more than 10% of the oil phase.

The term "emulsifier" refers to emulsifying agent used both to promote emulsification at the time of manufacture and to control stability of OF. In practice, combinations of emulsifiers rather than single agents are used. The emulsifier also influences the surface properties of the droplets and on the droplet size distributions act to prevent or delay the various destabilization processes.

Emulsifying agents are classified into three groups: i) a specific class of emulsifiers (surface active agents); ii) macromolecular polymers from the following groups: polysaccharides, protein, glycoside, phospholipid, sterol derivative; and iii) finely divided solids as bentonite, veegum, aluminuim hydroxide.

According to certain embodiment, the oily based and liquid flavors are part of the emulsion thus improving retention in the film and preventing oiliness from those components.

According to certain embodiments, certain film forming polymer(s) are emulsifying agent and are put during cannabinoids emulsification stage to thicken the continuous phase and act to prevent or delay the emulsion destabilization processes. Film former polymer(s)/emulsifier(s) include but are not limited to cellulose derivatives, starches, gums and/or mixtures thereof.

According to certain embodiments, the methods disclosed herein comprise the use of film former polymer(s)/emulsifier(s) in amounts no more than 50% of the oil phase (wt/wt), preferably no more than 20% of the oil phase, and more preferably no more than 10% of the oil phase.

According to certain embodiments, the methods disclosed herein comprise the use of surfactant(s) combined with film former polymer emulsifier(s) during the emulsification stage.

The term "surfactant" refers to surface-active agent(s) that possess both polar (hydrophilic) and non-polar (hydrophobic, lipophilic) characteristics in the same molecule. Emulsifying therefore emulsifying agents include group of surfactants capable of adsorbing to the oil-water interface and forming a protective coating around droplet in the oil/water mixture. For lipophilic active ingredients that are poorly soluble in water, the use of surfactants and emulsifiers reduces the interfacial tension between the aqueous medium and the lipophilic active(s) thereby increasing their solubility and water compatibility. The surfactants stabilize the dispersion of on immiscible liquid in another.

Examples of surfactants with long chain aliphatic amines or amine salts, partial esters of polyhydric alcohols, alcohol sulphates, hydrocarbon sulphonic acids, lecithin, or various commercial surfactant emulsifiers suitable for use in oral products include, but are not limited to, Tween™ and Span™, phospholipids (egg, soy, or dairy lecithin), amphiphilic proteins (eg, whey protein isolate, caseinate), and amphiphilic polysaccharides (eg, gum Arabic, modified starch).

According to some embodiments, other surfactants can also be used, in vivo, to enhance penetration and/or wettability of the film to promote adhesion, those surfactant include polysorbates (Tween™), sodium dodecyl sulfate (sodium lauryl sulfate), lauryl dimethyl amine oxide, cetyltrimethylammonium bromide (CTAB), polyethoxylated alcohols, polyoxyethylene sorbitan octoxynol (Triton X100™), N,N-dimethyldodecylamine-N-oxide, hexadecyltrimethylammonium bromide (HTAB), polyoxyl 10 lauryl ether, Brij 721™, bile salts (sodium deoxycholate, sodium cholate) polyoxyl castor oil (Cremophor™), nonylphenol ethoxylate (Tergitol™), cyclodextrins, lecithin, methylbenzethonium chloride (Hyamine™).

The surfactants used in OF formulations disclosed herein are blends of oil-soluble and water-soluble surfactants.

The emulsifying agents used in OF formulations are not limited to surfactants but also include amphiphilic polysaccharides (eg, gum Arabic, modified starch), amphiphilic proteins (eg, whey protein isolate, caseinate) and emulsion stabilizing polymers (eg methyl cellulose and hydroxypropyl methyl cellulose).

According to some aspect of the present disclosure, OFs can offer a standardized dosage form as well as easier and more convenient administration, transportation, handling, and storage. OFs administration help in mitigating risks of choking, while also alleviating some concern with product friability. OFs are taken with or without water. Taking OFs without water is due to their ability to dissolve and/or disintegrate relatively quickly in a relatively small amount of saliva to release the active(s) in the mouth or allow permeation of the active through the mucosa or in the Gastro intestinal tract (GIT). OFs by design promote patient and subject safety and acceptability. OFs provide an attractive route for delivering lipophilic actives such as cannabinoids whether derived or not from *Cannabis*. However, currently available films or wafers containing *Cannabis* extracts or *Cannabis* compounds lack consistency, acceptable taste, product dosage homogeneity, and good physical characteristics (e.g., non-stickiness, non-tackiness, uniform appearance, and ease of peeling from substrate). An additional challenge with the integration of cannabinoids in OFs arise from their typically viscous oils or resinous characteristic when in concentrated forms at room temperature and normal pressure. This presents some additional difficulties for their incorporation into water-based formulations, such as OFs. The resulting cannabinoid films are often very sticky, and not easily handled and/or packaged, thus making the product not suitable for large scale production or unavailable at a commercially acceptable price. Example of such OF formulations are given in Tables 1 and 2. Formulations 1 and 3 are examples of a montelukast- and THC-containing OF, both formulated without the inclusion of a carrier oil. Both OF formulations 1 and 3 are characterized to be sticky. On the other hand, Formulations 2 formulated with montelukast alone and with the presence of carrier oil and formulation 4 formulated THC diluted in a carrier oil are examples of non-sticky OFs Montelukast, although lipophilic according to its Log P result in a non-sticky OF. The OF also allows the incorporation of a large amount of oil and without impacting the desired the non-stickiness character of the OF.

According to some aspect of the present disclosure, OF disclosed herein are designed to incorporates lipophilic actives including lipophilic cannabinoids such as THC which is a viscous oil, with high lipid solubility and low aqueous solubility, in water-based OF formulations by diluting the cannabinoid in a carrier oil and dispersing in water using surfactants. The carrier oil reduces the overall viscosity of cannabinoid mixture or extract, making it easier to handle and incorporate in water-based OF formulations. The presence of carrier oil in the formulation resulted in reducing film stickiness or adhesiveness, making the film suitable for large scale production and commercial exploitation. An example of lower adhesiveness (adhesiveness is understood as the ability of the film to adhere to surfaces) OF formulations is illustrated in Formulations 2 and 4, Tables 1 and 2.

TABLE 1

An OF formulation containing Montelukast.

| | Formulation 1-sticky OFs | | Formulation 2-non-sticky OFs | |
|---|---|---|---|---|
| Excipient | (% wt/wt) Wet Blend | (% wt/wt) Dry Film | (% wt/wt) Wet Blend | (% wt/wt) Dry Film |
| Water | 82.03 | — | 79.82 | — |
| Pullulan | 9.60 | 53.41 | 9.53 | 47.27 |
| Xanthan gum | 0.08 | 0.45 | 0.08 | 0.45 |
| Locust bean gum | 0.08 | 0.45 | 0.08 | 0.45 |
| Carrageenan | 0.80 | 4.50 | 0.80 | 4.50 |
| Sucralose | 1.09 | 6.01 | 1.09 | 5.34 |
| Glycerin | 1.92 | 10.68 | 1.91 | 9.36 |
| Sorbitol | 0.64 | 3.56 | 0.64 | 3.09 |
| Tween 80 | 1.23 | 6.85 | 1.22 | 5.95 |
| Span 80 | 0.72 | 4.00 | 0.71 | 3.57 |
| Montelukast | 1.81 | 10.09 | 2.06 | 10.01 |
| MCT Oil | 0 | 0 | 2.06 | 10.01 |
| Total Mass | 100 | 100 | 100 | 100 |

TABLE 2

An OF formulation containing THC (extracted and purified from cannabis plant).

| | Formulation 3-sticky OFs | | Formulation 4-non-sticky OFs | |
|---|---|---|---|---|
| Excipient | (% wt/wt) Wet Blend | (% wt/wt) Dry Film | (% wt/wt) Wet Blend | (% wt/wt) Dry Film |
| Water | 82.03 | — | 79.82 | — |
| Pullulan | 9.60 | 53.41 | 9.53 | 47.27 |
| Xanthan gum | 0.08 | 0.45 | 0.08 | 0.45 |
| Locust bean gum | 0.08 | 0.45 | 0.08 | 0.45 |
| Carrageenan | 0.80 | 4.50 | 0.80 | 4.50 |
| Sucralose | 1.09 | 6.01 | 1.09 | 5.34 |
| glycerin | 1.92 | 10.68 | 1.91 | 9.36 |
| Sorbitol | 0.64 | 3.56 | 0.64 | 3.09 |
| Tween 80 | 1.23 | 6.85 | 1.22 | 5.95 |
| Span 80 | 0.72 | 4.00 | 0.71 | 3.57 |
| THC | 1.81 | 10.09 | 2.06 | 10.01 |
| MCT Oil | 0 | 0 | 2.06 | 10.01 |
| Total Mass | 100 | 100 | 100 | 100 |

According to embodiments, viscous THC oil with high lipid solubility and low aqueous solubility, is incorporated in water-based formulations such as OFs by first diluting/dissolving the THC in a carrier oil, and then using surfactant(s) to disperse the oil in water.

Dispersing the oil in water using surfactants results in an oil-in-water emulsion. An emulsion is generally defined as two immiscible liquids with one of the liquids being dispersed as spherical droplets within the other. When the two liquids are oil and water and when the oil phase is dispersed in the water phase, the system is called an oil-in-water emulsion. The emulsion based film technique permit a control of the film content by locking in the components in a uniform way within the emulsified film matrix. Once cast and dried, the emulsion based matrix retain the film components in uniformed way which improved the film content uniformity as compared with OF made using other OF making techniques.

Known techniques have been disclosed for making micelle based cannabinoid OF, however, the process of making micelle is highly dependent on the actual concentration of molecules including the solvent which plays an integral part in the formation of micelles. This latter aspect of the required ratio to make uniform micelle render this technique deficient for the making of continuously cast OF, as the removal of the solvent in the casting and drying portion of the process will inevitably result in the alteration of the critical ratio and thus likely to lead to content uniformity issued. Content uniformity has been documented as being one of the most important aspect of OF making to permit the OF to be used as precise dosing for both lipophilic actives and specifically for the cannabinoid subset of the lipophilic active class of active compounds. Emulsion as opposed to micelle are suitable for OF.

Preparation of emulsions typically requires oil, water, surfactant(s) and or other emulsifying agent(s), and energy input. The energy input is commonly provided by mechanical forces applied to the system in the form of shear, turbulence, or cavitation, most commonly using high-pressure homogenization or sonication devices. These are high-energy methods that generate intense disruptive forces that mechanically breakup the oil phase into tiny droplets that are dispersed within the aqueous medium. There are a number of drawbacks in using high-energy methods (e.g., high-pressure homogenization or sonication devices) to produce emulsions, such as high equipment and operating costs and high power requirement. In the case of emulsions containing cannabinoids, an additional drawback to the use of high-energy methods is that they may jeopardize the stability cannabinoids such as THC and CBD. Therefore, to avoid the equipment operating costs and to minimize THC degradation, low-energy methods are preferred for generating cannabinoids emulsions. According to some embodiments, the emulsions are spontaneously formed without the application of mechanical forces. This is achieved with specific surfactant geometry and concentration, mixing conditions, addition rate, stirring speed and temperature.

For emulsion-based OFs disclosed herein, according to certain embodiments, the stability of the emulsion (during blending, casting, and drying) is necessary for yielding uniform OFs, in which the oil droplets remain emulsified and stabilized within the dry polymer film matrix. Emulsions can become unstable due to several physicochemical mechanisms (destabilization processes) such as flocculation, flotation, sedimentation, creaming, coalescence, Ostwald ripening and phase inversion. These destabilizing mechanisms are correlated; for example, there is an increase in particle size due to aggregation by flocculation, coalescence or Ostwald ripening. This results in an increase in droplet instability and thus leads to gravitational separation (creaming/flotation/sedimentation). Additionally, these processes may happen simultaneously, not only consecutively.

For OFs disclosed herein, according to certain embodiments, the composition and total amount of oil phase (i.e. carrier oil, lipophilic active(s), and oil-soluble surfactants and/or other emulsifiers) will generally impact both, the ability to initially create the emulsion within which the oil droplets are well dispersed in the aqueous phase, while typically also influencing the subsequent stabilization of the emulsion against destabilizing mechanisms (e.g., Ostwald ripening).

According to some embodiment, the viscosity delta, the difference between the viscosity of the aqueous phase and the viscosity of the oil phase in absolute value is lower than 5000 cps, preferably lower than 4000 cps, most preferably lower than 3000 cps.

Specifically, larger differences in the viscosity between the oil and the aqueous phases will hinder the emulsion formation and promote phase separation. The formulations disclosed herein thus preferably include viscosity modifying agents to increase the viscosity of the aqueous phase and improve the emulsion stability by diminishing the rise of the oil droplets to the surface. Table 3 contain examples of increasing the viscosity of an aqueous solution using glycerol/glycerine. Viscosity modifiers are added to the aqueous phase to increase the viscosity in and attempt to mitigate the difference in viscosity between the oil phase and the aqueous phases and thus promote emulsion stability.

Viscosity-modifiers include, but are not limited to, glycerol/glycerin, caprylic/capric triglyceride, propylene glycol dicaprate/dicaprylate, cetearyl alcohol, stearyl alcohol, behenyl alcohol, cetyl alcohol, hydrogenated castor oil, hydrogenated Shea butter, pectin, xanthan gum, acacia gum, carrageenan, cellulose gum, methyl cellulose, methyl ethyl cellulose, carboxy methyl cellulose, hydroxyl propyl cellulose, hydroxyl propyl methyl cellulose, hydroxyl ethyl cellulose, pullulan, polyvinylpyrrolidone, polyvinyl acetate, and poly ethylene oxide. The addition of film-forming polymers also increases the viscosity of the aqueous phase.

TABLE 3

Viscosity of aqueous glycerol solutions. The solutions were prepared by mixing calculated weights of glycerol and of MilliQ water. Viscosity was measured using a DV1 Viscometer (CAN-AM instruments LTD, model DV1MRVTB0, serial # 8697375) equipped with a SC4-21 spindle rotating at the specified values. Measurements were taken at room temperature (23.5° C.)

| % Glycerol (wt/wt) | Viscosity (cP) | Spindle Rotation (rpm) | Torque (%) |
|---|---|---|---|
| 0%* | 1.0 | N/A | N/A |
| 5% | 1.5 | 100 | 0.4 |
| 10% | 3.0 | 50 | 0.4 |
| 50% | 11.0 | 10 | 0.2 |
| 70% | 20.0 | 10 | 0.3 |
| 100% | 905.0 | 5 | 18.1 |

*Theoretical value.

In certain embodiments, viscosity-modifying agents are added in amounts no more than 10% (wt/wt) of the wet blend formulation, preferably no more than 5% (wt/wt) and more preferably no more than 2.5% (wt/wt).

The effect of viscosity difference (between oil dispersed phase and aqueous continuous phase) on emulsion stability was investigated by preparing oil-in-water emulsion samples of varying amount of glycerol added (between 0% and 5% [wt/wt] of blend). The destabilization characteristics of prepared emulsions were followed by visually monitoring changes in droplet sizes/distribution and occurrence of droplet flocculation, coalescence, flotation or sedimentation, using light microscopy. As seen in Table 4, the addition of glycerol improves the quality of prepared oil-in-water emulsions.

TABLE 4

Variation of emulsion stability with addition of a viscosity modifying agent to the aqueous phase. The emulsion consisted of melted cocoa butter emulsified with lecithin and homogenized in aqueous glycerol solutions at 5000 rpm for 3 minutes. The resulting oil in water emulsions were examined by light microscopy within 1 hour of their preparation.

| Viscosity | Emulsion Destabilization Characteristic | | | | |
|---|---|---|---|---|---|
| Modifying Agent % (wt/wt) | Droplet Size | Floccu-lation | Coa-lescence | Flota-tion | Sedimen-tation |
| 0% Glycerol | Mixed sizes | ✓ | ✓ | ✓ | — |
| 2.5% Glycerol | Mixed sizes | — | — | — | — |
| 4.0% Glycerol | Mixed sizes | ✓ | — | — | — |

The viscosity of lipophilic actives and cannabinoids, such as THC and *Cannabis* oils are generally much different (higher) than that of water. In addition to using viscosity-modifying agents to increase the overall viscosity of the aqueous phase, the disclosed formulations use the carrier oil/lipophilic surfactant(s) to reduce the overall viscosity of the *Cannabis* oil phase, promoting the production of improved stability all together making it easier to produce stable and uniformly distributed THC and *Cannabis* oil-in-water emulsions.

Additionally, in an oil-in-water emulsion, the higher the oil phase viscosity, the larger the minimum achievable droplet size and, therefore, the lower the kinetic stability of the emulsion. It is therefore important to identify an appropriate oil phase (carrier oil and lipophilic emulsifiers) to prepare stable emulsions, especially when applying low-energy methods. The effect of oil phase viscosity on emulsion stability was investigated by preparing oil-in-water emulsion samples of varying viscosity values. The emulsions were prepared using low-energy methods (mixing at 1000 rpm for 10 minutes). The destabilization characteristics of prepared emulsions were followed by monitoring changes in droplet sizes/distribution and occurrence of droplet flocculation, coalescence, flotation or sedimentation, using light microscopy. As seen in Table 5, the higher the oil phase viscosity, the larger the droplet size, and therefore the more unstable the resulting emulsion (seen as floating of oil droplets to the surface, cohesion between oil droplets, and finally to creaming and separation.

TABLE 5

Variation of emulsion stability with oil (dispersed) phase viscosity. The emulsion consisted of MCT oil emulsified with a mixture of Tween 80 and Span 80, and mixed in aqueous solution at 1000 rpm for 10 minutes. The resulting oil-in-water emulsions were examined by light microscopy within 1 hour of their preparation.

| Viscosity of | O/W Emulsion Destabilization Characteristic | | | | |
|---|---|---|---|---|---|
| oil (dispersed) phase | Droplet Size | Floccu-lation | Coa-lescence | Flota-tion | Sedimen-tation |
| 30.5 | Very small | — | — | ✓ | — |
| 35.0 | Very small | — | — | — | — |
| 50 | Small | — | — | — | — |
| 60 | Mixed sizes | — | ✓ | ✓ | — |

A lower viscosity for the oil (dispersed) phase can also be achieved by increasing the temperature. In some embodiments initial carrier oil was heated to 70-90° C. in other embodiments, the emulsified oil/surfactant(s) mixture was heated to 70-90° C.

As with oils, only certain types and combinations of surfactants/emulsifying agents are suitable for forming emulsions, spontaneously, without the application of high-energy methods. The choice of suitable surfactant(s) starts with determining the hydrophobic lipophilic balance (HLB) value that matches that of the carrier oil in the formulation. The HLB value of a surfactant (or an oil) is a measure of the degree to which it is hydrophilic or lipophilic, determined by calculating values for the different regions of the molecule. In the formulations disclosed herein, the HLB values are chosen so that the surfactants are hydrophilic but able to be soluble in the oil phase. A combination of small-molecule surfactants (such as polysorbate and sorbitan) and phospholipids (such as phosphatidylserine, phosphatidylethanolamine, phosphatidylcholine, and sphingomyelins, egg/soy/dairy lecithin) are found to be the most effective for emulsifying lipophilic active(s) in formulations disclosed herein, using low-energy methods.

In some embodiments, one surfactant (with the same HLB value as the carrier oil) is used. In other embodiments a combination of surfactants (with low and high HLB values) are used.

The surfactant(s)/emulsifying agent(s) concentration is an important factor in the formation and stability of emulsions formed by low-energy methods. When applying low-energy methods (e.g., stir speed 200 to 500 rpm), a relatively high amount of surfactant (e.g., a 1:1 oil:surfactant ratio) is required. This can lead to cost, taste, and safety concerns. Similarly, an increased oil content in the emulsions requires higher amount of surfactant to stabilize an oil-in-water emulsion prepared by low-energy methods. With high content of lipophilic active(s), carrier oil, and surfactant(s) in the oil phase of the emulsion—and in the resulting OFs—it is critical to determine the optimal combination of oil phase components that can produce a stable oil-in-water emulsion while preserving the resulting OF physical/mechanical properties. In the formulations disclosed herein, the amount of surfactant/emulsifying agent required to spontaneously produce emulsions is reduced by using co-solvents (eg, glycerol, propylene glycol, and ethanol). Co-solvents can alter the bulk properties of aqueous solutions (eg, viscosity, see Table 2). The methods disclosed herein allow the use of surfactant(s) in amounts no more than 50% of the oil phase, preferably no more than 20% of the oil phase, and more preferably no more than 10% of the oil phase.

According to some embodiments, the emulsions disclosed herein are produced based on the spontaneous formation of small oil droplets in surfactant-oil-water system under specific environmental conditions (i.e., composition, temperature, stirring). The oil droplets are then trapped in a polymer matrix in the form of an OF. See example Formulation 5:

TABLE 6

| Formulation 5 Components | | |
|---|---|---|
| Formulation 5 Components | (% wt/wt) Wet Blend | (% wt/wt) Dry Film |
| Water | 79.42 | 0 |
| Pullulan | 9.53 | 46.32 |
| Xanthan gum | 0.08 | 0.39 |
| Locust bean gum | 0.08 | 0.39 |
| Carrageenan | 0.80 | 3.90 |
| Peppermint oil | 0.21 | 1.00 |
| Sucralose | 0.56 | 2.70 |
| glycerin | 1.91 | 9.26 |
| Sorbitol | 0.64 | 3.09 |
| Ascorbic acid | 0.41 | 2.00 |
| Tween 80 | 1.22 | 5.94 |
| Span 80 | 0.71 | 3.47 |
| THC | 2.06 | 10.01 |
| MCT Oil | 2.06 | 10.01 |

According to some embodiments, spontaneous formation of emulsions is attractive because it does not require the use of any specialized homogenization equipment which makes the process more economically efficient and less time consuming when compared with emulsions requiring the use of homogenizer. However, a number of important factors related to the preparation conditions (mixing conditions, addition rate, stirring speed and temperature), must be taken into account to produce stable emulsions, spontaneously. The presently disclosed emulsions are preferably made by mixing the lipophilic active with the carrier oil and other components of the oil phase. It is preferred to ensure homogeneity of the oil phase prior to mixing the oil phase with the aqueous phase. The oil phase is expected to be adequately mixed prior to the combination of the oil and aqueous phases.

According to some embodiments, the lipophilic actives are mixed with the carrier oil and the surfactant(s) and other emulsifying agent(s) and stabilizers. The components (lipophilic active(s), carrier oil and emulsifiers) of this oil phase are stirred together to mitigate potential uniformity issues.

According to some embodiments, the oil phase is then titrated into the aqueous phase at a controlled rate until formation of small oil droplets is achieved. Constant mixing of stirring should be maintained for a period of no less than 60 minutes, preferably 30 minutes, and more preferably 15 minutes to reach expected droplet size and promote homogeneity of the oil in water emulsion.

The emulsified oil phase is titrated into the aqueous phase (100 g) at an addition rate of about 15 g per minute, more preferably 10 g per minute. During this addition/titration time, the mixture is continuously stirred at 800 rpm for 60 minutes, preferably 30 minutes, and more preferably 15 minutes.

According to other embodiment, the mixture is continuously stirred at speed of 800 to 3000 rpm, preferably 1000-2500 rpm, more preferably 1500-2000 rpm with respective time of from 90 to 15 minutes, 80 to 20 minutes, 60 to 40 minutes.

According to other embodiment, the emulsions are not formed spontaneously but rather produced by the input of high-energy (ie, homogenization) to result small, emulsified droplets in a stabilized oil-in-water system. These are then trapped in a polymer matrix in the form of an OF. See example formulations 6-11:

TABLE 7

Formulation 6 Components
Formulation 6

| Components | % Wet | % Dry |
|---|---|---|
| Water | 77.42 | — |
| Methanol | 0.36 | — |
| Glycerine | 1.23 | 5.51 |
| Hydroxylated lecithin | 1.52 | 6.84 |
| Gum Arabic | 1.15 | 5.16 |
| Hydroxy propyl methyl cellulose (low viscosity) | 0.64 | 2.88 |
| Xanthan gum | 0.14 | 0.62 |
| THC oil | 3.29 | 14.79 |
| Flavor oil | 2.33 | 10.48 |
| Ascorbic acid | 0.42 | 1.90 |
| Citric acid | 0.70 | 3.14 |
| Sweetener | 4.04 | 18.17 |
| Flavor enhancer | 0.42 | 1.90 |
| Bitter masker | 0.42 | 1.90 |
| Propylparaben | 0.02 | 0.10 |
| Carboxy methyl cellulose (high viscosity) | 2.32 | 10.45 |
| Carboxy methyl cellulose (low viscosity) | 3.59 | 16.16 |
| Total | 100.0 | 100.0 |
| Total Dry Mass | 22.23 | |

TABLE 8

Formulation 7 Components
Formulation 7

| Components | % Wet | % Dry |
|---|---|---|
| Water | 77.01 | — |
| Methanol | 0.36 | — |
| Glycerine | 1.22 | 5.38 |
| Hydroxylated lecithin | 1.51 | 6.68 |
| Gum Arabic | 1.14 | 5.04 |
| Hydroxy propyl methyl cellulose (low viscosity) | 0.64 | 2.82 |
| Xanthan gum | 0.14 | 0.60 |
| THC oil | 3.27 | 14.44 |
| Natural flavors | 2.84 | 12.56 |
| Ascorbic acid | 0.42 | 1.86 |
| Citric acid | 0.69 | 3.06 |
| Sweetener | 4.02 | 17.75 |
| Flavor enhancer | 0.42 | 1.86 |
| Bitter masker | 0.42 | 1.86 |
| Propylparaben | 0.02 | 0.09 |
| Carboxy methyl cellulose (high viscosity) | 2.31 | 10.21 |
| Carboxy methyl cellulose (low viscosity) | 3.57 | 15.78 |
| Total | 100.0 | 100.0 |
| Total Dry Mass | 22.63 | |

TABLE 9

Formulation 8 Components
Formulation 8

| Components | % Wet | % Dry |
|---|---|---|
| Water | 77.42 | — |
| Methanol | 0.36 | — |
| Glycerine | 1.23 | 5.51 |
| Hydroxylated lecithin | 1.52 | 6.84 |
| Gum Arabic | 1.15 | 5.16 |
| Hydroxy propyl methyl cellulose (low viscosity) | 0.64 | 2.88 |
| Xanthan gum | 0.14 | 0.62 |
| THC/CBD oil | 3.29 | 14.79 |
| Flavor oil | 2.33 | 10.48 |
| Ascorbic acid | 0.42 | 1.90 |
| Citric acid | 0.70 | 3.14 |
| Sweetener | 4.04 | 18.17 |
| Flavor enhancer | 0.42 | 1.90 |
| Bitter masker | 0.42 | 1.90 |
| Propylparaben | 0.02 | 0.10 |
| Carboxy methyl cellulose (high viscosity) | 2.32 | 10.45 |
| Carboxy methyl cellulose (low viscosity) | 3.59 | 16.16 |
| Total | 100.0 | 100.0 |
| Total Dry Mass | 22.23 | |

TABLE 10

Formulation 9 Components
Formulation 9

| Components | % Wet | % Dry |
|---|---|---|
| Water | 77.01 | — |
| Methanol | 0.36 | — |
| Glycerine | 1.22 | 5.38 |
| Hydroxylated lecithin | 1.51 | 6.68 |
| Gum Arabic | 1.14 | 5.04 |
| Hydroxy propyl methyl cellulose (low viscosity) | 0.64 | 2.82 |
| Xanthan gum | 0.14 | 0.60 |
| THC/CBD oil | 3.27 | 14.44 |
| Natural flavors | 2.84 | 12.56 |
| Ascorbic acid | 0.42 | 1.86 |
| Citric acid | 0.69 | 3.06 |
| Sweetener | 4.02 | 17.75 |

TABLE 10-continued

Formulation 9 Components
Formulation 9

| Components | % Wet | % Dry |
|---|---|---|
| Flavor enhancer | 0.42 | 1.86 |
| Bitter masker | 0.42 | 1.86 |
| Propylparaben | 0.02 | 0.09 |
| Carboxy methyl cellulose (high viscosity) | 2.31 | 10.21 |
| Carboxy methyl cellulose (low viscosity) | 3.57 | 15.78 |
| Total | 100.0 | 100.0 |
| Total Dry Mass | | 22.63 |

TABLE 11

Formulation 10 Components
Formulation 10

| Components | % Wet | % Dry |
|---|---|---|
| Water | 77.42 | — |
| Methanol | 0.36 | — |
| Glycerine | 1.23 | 5.51 |
| Hydroxylated lecithin | 1.52 | 6.84 |
| Gum Arabic | 1.15 | 5.16 |
| Hydroxy propyl methyl cellulose (low viscosity) | 0.64 | 2.88 |
| Xanthan gum | 0.14 | 0.62 |
| CBD oil | 3.29 | 14.79 |
| Flavor oil | 2.33 | 10.48 |
| Ascorbic acid | 0.42 | 1.90 |
| Citric acid | 0.70 | 3.14 |
| Sweetener | 4.04 | 18.17 |
| Flavor enhancer | 0.42 | 1.90 |
| Bitter masker | 0.42 | 1.90 |
| Propylparaben | 0.02 | 0.10 |
| Carboxy methyl cellulose (high viscosity) | 2.32 | 10.45 |
| Carboxy methyl cellulose (low viscosity) | 3.59 | 16.16 |
| Total | 100.0 | 100.0 |
| Total Dry Mass | | 22.23 |

TABLE 12

Formulation 11 Components
Formulation 11

| Components | % Wet | % Dry |
|---|---|---|
| Water | 77.01 | — |
| Methanol | 0.36 | — |
| Glycerine | 1.22 | 5.38 |
| Hydroxylated lecithin | 1.51 | 6.68 |
| Gum Arabic | 1.14 | 5.04 |
| Hydroxy propyl methyl cellulose (low viscosity) | 0.64 | 2.82 |
| Xanthan gum | 0.14 | 0.60 |
| CBD oil | 3.27 | 14.44 |
| Natural flavors | 2.84 | 12.56 |
| Ascorbic acid | 0.42 | 1.86 |
| Citric acid | 0.69 | 3.06 |
| Sweetener | 4.02 | 17.75 |
| Flavor enhancer | 0.42 | 1.86 |
| Bitter masker | 0.42 | 1.86 |
| Propylparaben | 0.02 | 0.09 |
| Carboxy methyl cellulose (high viscosity) | 2.31 | 10.21 |
| Carboxy methyl cellulose (low viscosity) | 3.57 | 15.78 |
| Total | 100.0 | 100.0 |
| Total Dry Mass | | 22.63 |

When high-energy methods are applied, the oil-in-water mixture is homogenized at speed of 1000 to 15000 rpm, preferably 5000 to 10000 rpm, more preferably 7000-8000 rpm, with respective time of from 90 to 2 minutes, 80 to 20 minutes, 60 to 10 minutes.

The aqueous phase, into which the oil phase is titrated, contains water and hydrophilic surfactant(s) and or other, emulsifying agent(s), and other emulsion stabilizer(s). According to some embodiments, it is desirable to add surfactants and stabilizers to the oil phase to aim at bridging the difference in viscosity between the oil and aqueous phases.

According to some embodiments, the aqueous phase may contain co-solvent(s) such as glycerol, propylene glycol, and ethanol.

Additionally, the aqueous phase may contain tonicity agent(s) such as sodium chloride, potassium chloride, mannitol and dextrose.

Additionally, the aqueous phase may contain viscosity modifying agent(s), such as glycerol/glycerin, caprylic/capric triglyceride, propylene glycol dicaprate/dicaprylate, cetearyl alcohol, stearyl alcohol, behenyl alcohol, cetyl alcohol, hydrogenated castor oil, hydrogenated Shea butter, and film forming polymers.

Co-solvent(s), tonicity agent(s) are used to promote formation of emulsions with small oil droplets, by modifying the dispersed oil phase and the continuous aqueous phase to have similar viscosities thereby facilitating the rapid movement of surfactant, oil, and water molecules (see Tables 2, 3, and 4). Small size of emulsified oil droplets is desirable because it helps stabilize the oil droplets within the polymer matrix during the drying process, resulting homogenous OFs in which the oil droplets are evenly distributed within the polymer matrix of the dry OF.

According to some embodiments, the OFs disclosed herein contain lipophilic active(s), more specifically lipophilic cannabinoids dispersed in a carrier oil and uniformly distributed in the continuously cast film as emulsified oil droplets into a polymer matrix.

According to some embodiments, the OFs disclosed herein contain amphiphilic active(s) dispersed in a carrier oil and uniformly distributed in the continuously cast film as emulsified oil droplets into a polymer matrix.

The term "matrix" or "film matrix" refers to the polymer component or mixture of polymers, which creates the film forming matrix supporting the API within the oral film dosage form.

The OFs contain, in addition to emulsified lipophilic active(s) and film-forming polymer(s), the following inactive ingredients or excipients: co-solvent such as glycerol, viscosity modifiers such as PEG, sweeteners such as sucralose, surfactants such as lecithin, and colorants or opacifiers such as titanium dioxide. The formulation may further include antimicrobial agents such as methylparaben or propylparaben, preservatives such as butylated hydroxyl toluene (BHT) or alpha-tocopherol, antioxidants such as citric acid or ascorbic acid, and metal chelators such as ethylenediaminetetraacetic acid (EDTA). The antimicrobial, preservatives, and antioxidants are used alone or in combination.

According to some embodiments, additional excipients (such as sweeteners, flavors, and taste masking agents) make less than 2.5% by weight preferably less than 1% by weight of the OF composition.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Useful flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, and the like may also be used. Further examples of aldehyde flavorings include, but are not limited to acetaldehyde (apple); benzaldehyde (cherry, almond); cinnamicaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape; mixtures thereof; and the like.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The amount of flavoring employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1 to about 5 wt are useful with the practice of the present invention.

Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenylglycine, L-aspartyl-2,5-dihydro-L-phenylalanine, L-aspartyl-L-(1-cyclohexyen)-alanine, and the like; water-soluble sweeteners derived from naturally occurring water-soluble sweeteners, such as a chlorinated derivatives of ordinary sugar (sucrose), known, for example, as sucralose; and protein based sweeteners such as *Thaurnatoccous danielli* (Thaurnatin I and II).

Also color additives can be used in preparing the OF. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments include, for example the oxides of iron or titanium. The oxides of iron or titanium are preferably added in concentrations ranging from about 0.001 to about 10%, and more preferably in amounts of about 0.5 to about 3%, based on the weight of all the components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, flow accelerators, mold release agents, granulating agents, diluents, binders, buffers, absorbents, glidants, adhesives, anti-adherents, acidulants, softeners, resins, demulcents, solvents, surfactants, emulsifiers; such as glycerol mono oleate, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses, hydroxyalkylcelluloses, and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethyl cellulose (HPMC); carboxyalkylcelluloses, carboxyalkylalkylcelluloses, carboxyalkylcellulose esters such as carboxymethylcellulose (CMC) and their alkali metal salts; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

According to some embodiments, OFs formed with an oil-in-water emulsion, the lipophilic active(s) are solubilized in the oil phase of an oil-in-water emulsion. The emulsion is mixed with film-forming polymers then casted and allowed to dry, forming OFs. Maintaining the emulsion stability (without droplet flocculation, coalescence, flotation, or sedimentation) during the blending and drying processes are critical for controlling both the content of lipophilic active(s) in the OF and the physical/mechanical properties of the films. The film matrix therefore must comprise an appropriate selection of excipients (see Formulation 1-21 below), which together can maintain the oil droplet composition as a homogenous dispersion, and prevents their aggregation and coalescence. When oil droplet aggregation is not controlled and prevented, the oil droplets size will grow and they will phase separate and desorb from the film matrix, thereby accumulating at the surface of the OF. As this occurs, the oil carrying the lipophilic active(s) will be lost to the OF packaging interior surfaces. This product when consumed will no longer meet the label claim API loading.

After blending the emulsion with the polymers and other inactive ingredients, OFs are manufactured by coating the blend as a thin sheet on a liner and drying the coated blend in an oven. According to some embodiment. The lab-scale drying temperature is between 20° C. and 90° C., preferably 30 and 85° C.; and more preferably, the drying temperature is 40 and 80° C.

The emulsion based OF also promote flavor retention and protection against evaporation which is often observed with volatile component such as flavors. Emulsion based oral film also mitigate flavor losses during the casting and drying techniques.

Emulsion destabilization (creaming, aggregation, and/or coalescence) during the drying process can affect the structure of the emulsion-based OFs by resulting in a concentrated oil layer at the OF surface. The presence or accumulation of an oil layer on the surface of OFs can be monitored by measuring the surface hydrophobicity using contact angle measurements (see Table 13). Contact angles measurements describe the surface hydrophobicity (see FIG. 3) and detect the formation of a concentrated oil layer at the OF surface. Contact angle measurements indicate the stability of oil emulsions in emulsion-based OFs.

TABLE 13

Summary of contact angle measurements of OFs containing various amounts of oil. The technique of contact angle measurement is a direct measurement of the tangent angle at the three-phase contact point on a sessile drop profile. A drop (10 μL of deionized water) is deposited on the OF surface while mounted on a horizontal stage. An image is recorded using a USB digital microscope, equipped with a 1000x continuous zoom. The recorded image is then analyzed using ImageJ free software, using the contact angle plugin.

| Film Content | Contact angle (degrees) |
| --- | --- |
| 0% oil (dry film, wt/wt) | 52 |
| 10% oil (dry film, wt/wt) | 49 |
| 20% oil (dry film, wt/wt) | 41 |
| 30% oil (dry film, wt/wt) | 39 |
| Teflon Reference hydrophobic surface | 102 |

Contact angles measurements describe the surface hydrophobicity (see FIG. 3) and detect the formation of a concentrated oil layer at the OF surface. Contact angle measurements indicate the stability of oil emulsions in emulsion-based OFs.

As seen in Table 13, following the fabrication methods disclosed herein results emulsion-based OFs containing emulsified oil droplets stabilized within the polymer matrix. Contact angle of less than 90 degrees were measured for OFs containing various amounts of oil. This indicates that the OF surface is hydrophilic (i.e., the emulsified oil droplets do not accumulate at the OF surface) and that the film matrix sufficiently stabilizes the oil droplets and prevents their aggregation and coalescing.

To further assess the accumulation of an oil layer on the OF surface, weight change was assessed upon drying off the top and bottom OF surfaces using cleaning wipes (Kimwipes® Low-Lint-1-Ply, 4.4×8.4"). Drying was accomplished by tightly wrapping the OF between the cleaning wipes, for at least 2 hours at either 23° C. or 40° C. (i.e., temperature representative of the OF drying conditions applied during the fabrication). This weight change assessment was performed on OFs fabricated using the methods disclosed herein. A reference OF with an oily surface (not fabricated according to excipients/methods disclosed here) was also assessed. As seen in Table 14, OFs weight change upon drying is below 5%, whereas the oily surface reference OF has weight changes up to 15%. This indicates that the OF fabrication methods disclosed herein results emulsion-based OFs containing emulsified oil droplets stabilized within the casted polymer matrix.

TABLE 14

Assessment of OF surface oiliness. The OF top and bottom surfaces were dried with cleaning wipes, and the OF weight change was measured. The OF was tightly wrapped with Kimwipes ® (Low-Lint -1-Ply, 4.4 × 8.4") for 2 hours.

Room Temperature Study (23° C.)

| Oil Content (dry film, wt/wt) | Initial weight | Final Weight | Weight change | Weight Change % |
| --- | --- | --- | --- | --- |
| 0% oil | 57 | 56.95 | −0.05 | 0.09 |
| 10% oil | 61.1 | 60.9 | −0.2 | 0.33 |
| 20% oil | 64.5 | 64.3 | −0.2 | 0.31 |
| 30% oil | 70.9 | 70.5 | −0.4 | 0.56 |
| 27% oil reference film | 172.8 | 161.51 | −11.29 | 6.53 |

Higher Temperature Study (40° C.)

| Formulation | Initial weight | Final Weight | Weight change | Weight Change % |
| --- | --- | --- | --- | --- |
| 0% oil | 60.03 | 58.3 | −1.73 | 2.88 |
| 10% oil | 71.16 | 69.14 | −2.02 | 1.41 |
| 20% oil | 64.2 | 62.4 | −1.8 | 2.80 |
| 30% oil | 76.03 | 74.02 | −2.01 | 2.64 |
| 27% oil reference film | 171.36 | 145.45 | −25.91 | 15.12 |

The OFs described herein are not sticky. They also do not have an oily feeling on the fingers. Most importantly, they are easy to handle and package, and are uniform in content and appearance.

The OFs described herein can be used for convenient delivery of lipophilic pharmaceutical active ingredients or other lipophilic nutritional agents, including essential oils and plant extracts.

According to other embodiments, HPMC was used to control the continuously cast OF oiliness once dried. Low viscosity HPMC was used to stabilize the OF emulsion as described in table 22, low HPMC promoted oil retention within the film matrix thereby preventing a loss of oil and mitigating the oiliness character of the film once cast and dried.

TABLE 15

Formulation 8 Components

| Formulation 8 | % Dry | % Wet |
|---|---|---|
| USP water |  | 77.00 |
| Lecithin | 6.60 | 1.52 |
| Glycerine | 7.00 | 1.61 |
| HPMC low viscosity | 33.00 | 7.59 |
| HPMC high viscosity | 9.15 | 2.10 |
| gum arabic | 6.60 | 1.52 |
| CBD extract | 11.00 | 2.53 |
| xantham gum | 0.55 | 0.13 |
| ascorbic acid | 1.50 | 0.35 |
| Citric Acid | 2.00 | 0.46 |
| Sweetener | 7.27 | 1.67 |
| Flavor** | 13.33 | 3.07 |
| Bitter masker | 1.10 | 0.25 |
| Salt | 0.90 | 0.21 |
| Total | 100 | 100 |

TABLE 16

Formulation 9 Components

| Formulation 9 | % Dry | % Wet |
|---|---|---|
| USP water |  | 77.00 |
| Lecithin | 7.40 | 1.70 |
| Sorbitol | 7.40 | 1.70 |
| Alginate low viscosity* | 37.06 | 8.52 |
| gum arabic | 7.40 | 1.70 |
| CBD extract | 11.00 | 2.53 |
| xantham gum | 0.60 | 0.14 |
| ascorbic acid | 1.91 | 0.44 |
| Citric acid | 2.00 | 0.46 |
| Sweetener | 7.83 | 1.80 |
| Flavor** | 15.03 | 3.46 |
| Bitter masker | 1.47 | 0.34 |
| Salt | 0.90 | 0.21 |
| Total | 100.00 | 100.00 |

TABLE 17

Formulation 10 Components

| Formulation 10 | % Dry | % Wet |
|---|---|---|
| USP water |  | 77.00 |
| Lecithin | 8.12 | 1.87 |
| Glycerine | 8.12 | 1.87 |
| HPMC low viscosity * | 9.02 | 2.07 |
| Alginate low viscosity* | 31.81 | 7.32 |
| CBD extract | 14.66 | 3.37 |
| xantham gum | 0.68 | 0.16 |
| Ascorbic acid | 1.00 | 0.23 |
| Citric acid | 1.03 | 0.24 |
| Sweetener | 13.60 | 3.13 |
| Flavor** | 8.68 | 2.00 |
| Bitter masker | 2.26 | 0.52 |
| Salt | 1.02 | 0.23 |
| Total | 100 | 100 |

TABLE 18

Formulation 11 Components

| Formulation 11 | % Dry | % Wet |
|---|---|---|
| USP water |  | 77.0 |
| Lecithin | 7.02 | 1.61 |
| Glycerine | 2.73 | 0.63 |
| HPMC low viscosity | 11.7 | 2.69 |
| Alginate low viscosity | 27.50 | 6.33 |
| CBD extract | 12.68 | 2.92 |
| xantham gum | 0.59 | 0.14 |
| Ascorbic acid | 1.26 | 0.29 |
| Citric acid | 0.50 | 0.12 |
| Sweetener | 15.65 | 3.60 |
| Flavor | 17.56 | 4.04 |
| Bitter masker | 1.95 | 0.45 |
| Salt | 0.86 | 0.20 |
| Total | 100 | 100 |

TABLE 19

Formulation 12 Components

| Formulation 12 | % Dry | %Wet |
|---|---|---|
| USP water |  | 80.00 |
| Lecithin | 7.00 | 1.40 |
| Glycerine | 4.78 | 0.96 |
| HPMC low viscosity | 3 | 0.60 |
| CMC low viscosity | 27.00 | 5.40 |
| gum arabic | 5.11 | 1.02 |
| CBD extract | 12.50 | 2.50 |
| xantham gum | 0.60 | 0.12 |
| Ascorbic acid | 1.70 | 0.34 |
| Citric ac | 3.11 | 0.62 |
| Sweetener | 15.50 | 3.10 |
| Flavor | 17.00 | 3.40 |
| Bitter masker | 1.90 | 0.38 |
| Salt | 0.80 | 0.16 |
| Total | 100.00 | 100.00 |

TABLE 20

Formulation 13 Components

| Formulation 13 | % Dry | % Wet |
|---|---|---|
| USP water |  | 83.00 |
| Lecithin | 6.81 | 1.16 |
| Glycerine | 4.73 | 0.80 |
| HPMC low viscosity | 3.78 | 0.64 |
| Alginate low viscosity | 20.94 | 3.56 |
| CMC low viscosity | 9.37 | 1.59 |
| CBD extract | 12.30 | 2.09 |
| xantham gum | 0.57 | 0.10 |
| Ascorbic acid | 1.70 | 0.29 |
| Citric acid | 2.84 | 0.48 |
| Sweetener | 15.18 | 2.58 |
| Flavor** | 19.04 | 3.24 |
| Bitter masker | 1.89 | 0.32 |
| Salt | 0.85 | 0.14 |
| Total | 100.00 | 100.00 |

TABLE 21

Formulation 14 Components

| Formulation 14 | % Dry | % Wet |
|---|---|---|
| USP water |  | 83.00 |
| Lecithin | 6.81 | 1.16 |
| Glycerine | 4.73 | 0.80 |

TABLE 21-continued

Formulation 14 Components

| Formulation 14 | % Dry | % Wet |
|---|---|---|
| HPMC low viscosity | 4 | 0.68 |
| Alginate low viscosity | 18.00 | 3.06 |
| CMC low viscosity | 8.50 | 1.45 |
| Povidone | 5.00 | 0.85 |
| CBD extract | 12.30 | 2.09 |
| xantham gum | 0.50 | 0.09 |
| Citric acid | 1.70 | 0.29 |
| Sweetener | 2.84 | 0.48 |
| Sweetener | 15.18 | 2.58 |
| Flavor | 19.04 | 3.24 |
| Bitter masker | 1.40 | 0.24 |
| Total | 100 | 17.00 |

TABLE 22

Summary of oiliness for formulations 8-14

| Formulations | Oiliness | Comments |
|---|---|---|
| Formulation 8 | Oil free film | HPMC allows to improve emulsification |
| Formulation 9 | Oily film | No HPMC to better emulsify |
| Formulation 10 | Oil free film | |
| Formulation 11 | Oily film | combined HPMC of very low viscosity |
| Formulation 12 | Oily film | combined HPMC of very low viscosity |
| Formulation 13 | Oil free film | adjusted viscosity of HPMC together with CMC |
| Formulation 14 | Oil free film | adjusted viscosity of HPMC together with CMC |

According to embodiments, the OF or oral film dosage form comprises more than 20%, more than 25%, more than 30%, more than 35% or more than 40% (wt/wt) of oil.

According to embodiments more than 20%, more than 25%, more than 30%, more than 35% or more than 40% of the total composition of the OF formulation (wt/wt) is a combination of carrier oil and one or a mixture of cannabinoids.

According to embodiments, OF formulations comprise more of the carrier oil than of the lipophilic active or mixture of lipophilic actives.

According to some embodiments, it is disclosed an OCF consisting of: cannabinoids, cannabinoid extracts, cannabinoids derivatives resulting a food grade product.

According to some embodiment, the high oil content OFs have hydrophobic contact angles. High oil content film (up to 40%) have contact angle lower than 90 degrees, preferably lower than 70 degrees, more preferably lower than 50 degrees.

The stability of THC in OFs was assessed by determining the THC content after 1- and 2-week incubation in a 50° C. chamber. THC content was determined by dissolving the OFs in an ethanol/water mixture and injecting the resulting solution in a chromatographic system with the following conditions: instrument is HPLC Waters 2695 or equivalent, column is INERTSUSTAIN C18 HP 3 μm 150×4.6 mm or equivalent, detector is UV, detector wavelength is 228 nm, mobile phase is 45% methanol/25% water/20% tetrahydrofuran/10% acetonitrile. OF formulations used in this stability study are described in Table 23 and the THC stability results are summarized in Table 24.

The stability of THC substantially increases when included in a OF formulation compared to when diluted in a carrier oil.

The stability of THC in OFs increases with the use of a stabilizer, such as ascorbic acid. The stability of THC in OFs further increases with the use of a carrier oil, such as MCT oil.

TABLE 23

OF formulations examined for API (THC) stability

| | Formulation 15 | | Formulation 16 | | Formulation 17 | |
|---|---|---|---|---|---|---|
| Excipient | (% wt/wt) Wet Blend | (% wt/wt) Dry Film | (% wt/wt) Wet Blend | (% wt/wt) Dry Film | (% wt/wt) Wet Blend | (% wt/wt) Dry Film |
| Water | 82.03 | 0 | 81.66 | 0 | 79.42 | 0 |
| Pullulan | 9.60 | 53.41 | 9.55 | 52.09 | 9.53 | 46.32 |
| Xanthan gum | 0.08 | 0.45 | 0.08 | 0.43 | 0.08 | 0.39 |
| Locust bean gum | 0.08 | 0.45 | 0.08 | 0.43 | 0.08 | 0.39 |
| Carrageenan | 0.80 | 4.50 | 0.80 | 4.34 | 0.80 | 3.90 |
| Peppermint oil | 0.21 | 1.16 | 0.21 | 1.13 | 0.21 | 1.00 |
| Sucralose | 0.56 | 3.12 | 0.56 | 3.04 | 0.56 | 2.70 |
| glycerin | 1.92 | 10.68 | 1.91 | 10.06 | 1.91 | 9.26 |
| Sorbitol | 0.64 | 3.56 | 0.64 | 3.47 | 0.64 | 3.09 |
| Ascorbic acid | 0 | 0 | 0.41 | 2.26 | 0.41 | 2.00 |
| Tween 80 | 1.23 | 6.85 | 1.23 | 6.68 | 1.22 | 5.94 |
| Span 80 | 0.72 | 4.00 | 0.72 | 3.91 | 0.71 | 3.47 |
| THC | 1.81 | 10.09 | 1.84 | 10.06 | 2.06 | 10.01 |
| MCT Oil | 0 | 0 | 0 | 0 | 2.06 | 10.01 |
| Total Mass | 100 | 100 | 100 | 100 | 100 | 100 |

TABLE 24

Summary of THC stability data in OF formulations 15, 16, and 17.

| Formulation | THC Content* loss (%) | |
|---|---|---|
| | 1 Week/50° C. | 2 Week/50° C. |
| Reference: THC in MCT oil | 62 | 72 |
| Formulation 15 | 8 | 67 |
| Formulation 16 | 13 | 18 |
| Formulation 17 | —* | —* |

Calculated relative to THC content at T0
*negligible loss, no loss measured.

The following are examples of formulations for lipophilic active-emulsion based OFs.

TABLE 25

The formulation in example 11.
Formulation 18

| Components | % Wet | % Dry |
|---|---|---|
| Water | 76.42 | — |
| Pullulan (MW: 200,000) | 12.43 | 52.71 |
| Xanthan gum | 0.15 | 0.64 |
| Glycerin | 1.24 | 5.26 |
| Sorbitol | 1.24 | 5.26 |
| Tween 80 | 2.48 | 10.52 |
| Sucralose | 0.96 | 4.07 |
| Peppermint oil | 0.25 | 1.06 |
| MCT oil | 2.48 | 10.52 |
| Synthetic THC | 2.35 | 9.97 |
| Total | 100.00 | 100.00 |
| Total Dry Mass | 23.58 | |

TABLE 26

The formulation in example 12
Formulation 19

| Components | % Wet | % Dry |
|---|---|---|
| Water | 76.78 | — |
| Glycerin | 1.53 | 6.60 |
| Sucralose | 0.92 | 3.94 |
| Ammonium Glycyrrhizate | 0.46 | 1.97 |
| Flavor herb oil | 0.24 | 1.03 |
| Tween 80 | 1.45 | 6.24 |
| Span 80 | 0.87 | 3.74 |
| Microcrystalline cellulose | 3.60 | 12.16 |
| Hydroxy propyl cellulose (MW: 200,000) | 9.80 | 45.60 |
| MCT oil | 2.61 | 11.23 |
| CBD oil | 1.74 | 7.49 |
| Total | 100.00 | 100.00 |
| Total Dry Mass | 23.22 | |

TABLE 27

Formulation in Example 13
Formulation 20

| Components | % Wet | % Dry |
|---|---|---|
| Water | 78.41 | — |
| Hydrogenated Castor Oil | 1.13 | 5.23 |
| Pectin | 6.36 | 29.47 |
| Acacia gum | 0.82 | 3.80 |

TABLE 27-continued

Formulation in Example 13
Formulation 20

| Components | % Wet | % Dry |
|---|---|---|
| Sucralose | 0.82 | 3.80 |
| Hydroxylated Lecithin (Yelkin 1018) | 2.20 | 10.17 |
| Cannabis Extract | 10.26 | 47.53 |
| Total | 100.00 | 100.00 |
| Total Dry Mass | 21.59 | |

TABLE 28

Formulation in Example 14
Formulation 21

| Components | % Wet | % Dry |
|---|---|---|
| Water | 71.84 | — |
| Ultralec-P | 0.29 | 1.02 |
| Polyethylene glycol 400 | 2.16 | 7.65 |
| Hydroxypropyl cellulose | 10.78 | 38.27 |
| Hydroxypropylmethyl cellulose E5 | 1.44 | 5.10 |
| Hydroxypropylmethyl cellulose E50 | 0.72 | 2.55 |
| Polyethylene oxide N80 | 1.80 | 6.38 |
| Soy Bean Oil | 5.39 | 19.13 |
| Pemulen | 0.22 | 0.77 |
| Cannabis Extract | 5.39 | 19.13 |
| Total | 100.00 | 100.00 |
| Total Dry Mass | 28.16 | |

TABLE 29

Formulation in Example 15
Formulation 22

| Components | % Wet | % Dry |
|---|---|---|
| Water | 80.97 | — |
| Pectin | 6.60 | 34.65 |
| Microcrystalline cellulose (Avicel PH-105 NF I) | 0.84 | 4.42 |
| Glycerine | 4.21 | 22.11 |
| Sucralose | 1.26 | 6.62 |
| hydroxylated Lecithin (Yelkin 1018) | 1.14 | 5.97 |
| Cocoa butter | 1.93 | 10.13 |
| Acesulfame Potassium | 0.63 | 3.31 |
| Cannabis Extract | 1.93 | 10.13 |
| Sodium Chloride | 0.51 | 2.66 |
| Total | 100.00 | 100.00 |
| Total Dry Mass | 19.03 | |

TABLE 30

Formulation in Example 16
Formulation 23

| Components | % Wet | % Dry |
|---|---|---|
| Water | 69.55 | — |
| Glycerine | 1.39 | 4.57 |
| Sucralose | 0.83 | 2.74 |
| Polysorbate 80 | 1.32 | 4.34 |
| Sorbitan Oleate 80 | 0.79 | 2.60 |
| Peppermint Oil | 0.22 | 0.72 |
| Magnasweet | 0.42 | 1.37 |
| MCT Oil | 3.96 | 13.02 |

TABLE 30-continued

Formulation in Example 16
Formulation 23

| Components | % Wet | % Dry |
|---|---|---|
| Microcrystalline Cellulose (Avicel PH-105 NF I) | 11.96 | 39.29 |
| Hydroxypropyl cellulose | 4.45 | 14.62 |
| Ascorbic acid | 0.35 | 1.14 |
| Pullulan (MW: 200,000) | 2.78 | 9.14 |
| Cannabis Extract | 1.96 | 6.44 |
| Total | 100.00 | 100.00 |
| Total Dry Mass (g) | | 30.45 |

TABLE 31

The formulation in example 17.
Formulation 24

| Components | % Wet | % Dry |
|---|---|---|
| Water | 76.42 | — |
| Pullulan (MW: 200,000) | 12.43 | 52.71 |
| Xanthan gum | 0.15 | 0.64 |
| Glycerin | 1.24 | 5.26 |
| Sorbitol | 1.24 | 5.26 |
| Tween 80 | 2.48 | 10.52 |
| Sucralose | 0.96 | 4.07 |
| Peppermint oil | 0.25 | 1.06 |
| MCT oil | 2.48 | 10.52 |
| Montelukast freebase | 2.35 | 9.97 |
| Total | 100.00 | 100.00 |
| Total Dry Mass | | 23.58 |

TABLE 32

The formulation in example 18
Formulation 25

| Components | % Wet | % Dry |
|---|---|---|
| Water | 76.78 | — |
| Glycerin | 1.53 | 6.60 |
| Sucralose | 0.92 | 3.94 |
| Ammonium Glycyrrhizate | 0.46 | 1.97 |
| Flavor herb oil | 0.24 | 1.03 |
| Tween 80 | 1.45 | 6.24 |
| Span 80 | 0.87 | 3.74 |
| Microcrystalline cellulose | 3.60 | 12.16 |
| Hydroxy propyl cellulose (MW: 200,000) | 9.80 | 45.60 |
| MCT oil | 2.61 | 11.23 |
| Montelukast freebase | 1.74 | 7.49 |
| Total | 100.00 | 100.00 |
| Total Dry Mass | | 23.22 |

TABLE 33

Formulation in Example 19
Formulation 26

| Components | % Wet | % Dry |
|---|---|---|
| Water | 78.41 | — |
| Hydrogenated Castor Oil | 1.13 | 5.23 |
| Pectin | 6.36 | 29.47 |
| Guar gum | 0.82 | 3.80 |
| Sucralose | 0.82 | 3.80 |

TABLE 33-continued

Formulation in Example 19
Formulation 26

| Components | % Wet | % Dry |
|---|---|---|
| Hydroxylated Lecithin (Yelkin 1018) | 2.20 | 10.17 |
| Montelukast freebase | 10.26 | 47.53 |
| Total | 100.00 | 100.00 |
| Total Dry Mass | | 21.59 |

TABLE 34

Formulation in Example 20
Formulation 27

| Components | % Wet | % Dry |
|---|---|---|
| Water | 71.84 | — |
| Ultralec-P | 0.29 | 1.02 |
| Polyethylene glycol 400 | 2.16 | 7.65 |
| Hydroxypropyl cellulose | 10.78 | 38.27 |
| Hydroxypropylmethyl cellulose E5 | 1.44 | 5.10 |
| Hydroxypropylmethyl cellulose E50 | 0.72 | 2.55 |
| Polyethylene oxide N80 | 1.80 | 6.38 |
| Soy Bean Oil | 5.39 | 19.13 |
| Pemulen | 0.22 | 0.77 |
| Montelukast freebase | 5.39 | 19.13 |
| Total | 100.00 | 100.00 |
| Total Dry Mass | | 28.16 |

TABLE 35

Formulation in Example 21
Formulation 28

| Components | % Wet | % Dry |
|---|---|---|
| Water | 80.97 | — |
| Pectin | 6.60 | 34.65 |
| Microcrystalline cellulose (Avicel PH-105 NF I) | 0.84 | 4.42 |
| Glycerine | 4.21 | 22.11 |
| Sucralose | 1.26 | 6.62 |
| hydroxylated Lecithin (Yelkin 1018) | 1.14 | 5.97 |
| Cocoa butter | 1.93 | 10.13 |
| Acesulfame Potassium | 0.63 | 3.31 |
| Montelukast freebase | 1.93 | 10.13 |
| Sodium Chloride | 0.51 | 2.66 |
| Total | 100.00 | 100.00 |
| Total Dry Mass | | 19.03 |

TABLE 36

Formulation in Example 22
Formulation 29

| Components | % Wet | % Dry |
|---|---|---|
| Water | 69.55 | — |
| Glycerine | 1.39 | 4.57 |
| Sucralose | 0.83 | 2.74 |
| Polysorbate 80 | 1.32 | 4.34 |
| Sorbitan Oleate 80 | 0.79 | 2.60 |
| Peppermint Oil | 0.22 | 0.72 |
| Magnasweet | 0.42 | 1.37 |
| MCT Oil | 3.96 | 13.02 |

TABLE 36-continued

Formulation in Example 22
Formulation 29

| Components | % Wet | % Dry |
|---|---|---|
| Microcrystalline Cellulose (Avicel PH-105 NF I) | 11.96 | 39.29 |
| Hydroxypropyl cellulose | 4.45 | 14.62 |
| Ascorbic acid | 0.35 | 1.14 |
| Pullulan (MW: 200,000) | 2.78 | 9.14 |
| Montelukast freebase | 1.96 | 6.44 |
| Total | 100.00 | 100.00 |
| Total Dry Mass (g) | | 30.45 |

TABLE 37

The formulation in example 23.
Formulation 30

| Components | % Wet | % Dry |
|---|---|---|
| Water | 76.42 | — |
| Pullulan (MW: 200,000) | 12.43 | 52.71 |
| Xanthan gum | 0.15 | 0.64 |
| Glycerin | 1.24 | 5.26 |
| Sorbitol | 1.24 | 5.26 |
| Tween 80 | 2.48 | 10.52 |
| Sucralose | 0.96 | 4.07 |
| Peppermint oil | 0.25 | 1.06 |
| MCT oil | 2.48 | 10.52 |
| Tamoxifen | 2.35 | 9.97 |
| Total | 100.00 | 100.00 |
| Total Dry Mass | | 23.58 |

TABLE 38

The formulation in example 24
Formulation 31

| Components | % Wet | % Dry |
|---|---|---|
| Water | 76.78 | — |
| Glycerin | 1.53 | 6.60 |
| Sucralose | 0.92 | 3.94 |
| Ammonium Glycyrrhizate | 0.46 | 1.97 |
| Flavor herb oil | 0.24 | 1.03 |
| Tween 80 | 1.45 | 6.24 |
| Span 80 | 0.87 | 3.74 |
| Microcrystalline cellulose | 3.60 | 12.16 |
| Hydroxy propyl cellulose (MW: 200,000) | 9.80 | 45.60 |
| MCT oil | 2.61 | 11.23 |
| Tamoxifen | 1.74 | 7.49 |
| Total | 100.00 | 100.00 |
| Total Dry Mass | | 23.22 |

TABLE 39

Formulation in Example 25
Formulation 32

| Components | % Wet | % Dry |
|---|---|---|
| Water | 78.41 | — |
| Hydrogenated Castor Oil | 1.13 | 5.23 |
| Pectin | 6.36 | 29.47 |
| Guar gum | 0.82 | 3.80 |
| Sucralose | 0.82 | 3.80 |

TABLE 39-continued

Formulation in Example 25
Formulation 32

| Components | % Wet | % Dry |
|---|---|---|
| Hydroxylated Lecithin (Yelkin 1018) | 2.20 | 10.17 |
| Tamoxifen | 10.26 | 47.53 |
| Total | 100.00 | 100.00 |
| Total Dry Mass | | 21.59 |

TABLE 40

Formulation in Example 26
Formulation 33

| Components | % Wet | % Dry |
|---|---|---|
| Water | 71.84 | — |
| Ultralec-P | 0.29 | 1.02 |
| Polyethylene glycol 400 | 2.16 | 7.65 |
| Hydroxypropyl cellulose | 10.78 | 38.27 |
| Hydroxypropylmethyl cellulose E5 | 1.44 | 5.10 |
| Hydroxypropylmethyl cellulose E50 | 0.72 | 2.55 |
| Polyethylene oxide N80 | 1.80 | 6.38 |
| Soy Bean Oil | 5.39 | 19.13 |
| Pemulen | 0.22 | 0.77 |
| Tamoxifen | 5.39 | 19.13 |
| Total | 100.00 | 100.00 |
| Total Dry Mass | | 28.16 |

TABLE 41

Formulation in Example 27
Formulation 34

| Components | % Wet | % Dry |
|---|---|---|
| Water | 80.97 | — |
| Pectin | 6.60 | 34.65 |
| Microcrystalline cellulose (Avicel PH-105 NF I) | 0.84 | 4.42 |
| Glycerine | 4.21 | 22.11 |
| Sucralose | 1.26 | 6.62 |
| hydroxylated Lecithin (Yelkin 1018) | 1.14 | 5.97 |
| Cocoa butter | 1.93 | 10.13 |
| Acesulfame Potassium | 0.63 | 3.31 |
| Tamoxifen | 1.93 | 10.13 |
| Sodium Chloride | 0.51 | 2.66 |
| Total | 100.00 | 100.00 |
| Total Dry Mass | | 19.03 |

TABLE 42

Formulation in Example 28
Formulation 35

| Components | % Wet | % Dry |
|---|---|---|
| Water | 69.55 | — |
| Glycerine | 1.39 | 4.57 |
| Sucralose | 0.83 | 2.74 |
| Polysorbate 80 | 1.32 | 4.34 |
| Sorbitan Oleate 80 | 0.79 | 2.60 |
| Peppermint Oil | 0.22 | 0.72 |
| Magnasweet | 0.42 | 1.37 |
| MCT Oil | 3.96 | 13.02 |

TABLE 42-continued

Formulation in Example 28
Formulation 35

| Components | % Wet | % Dry |
|---|---|---|
| Microcrystalline Cellulose (Avicel PH-105 NF I) | 11.96 | 39.29 |
| Hydroxypropyl cellulose | 4.45 | 14.62 |
| Ascorbic acid | 0.35 | 1.14 |
| Pullulan (MW: 200,000) | 2.78 | 9.14 |
| Tamoxifen | 1.96 | 6.44 |
| Total | 100.00 | 100.00 |
| Total Dry Mass (g) | 30.45 | |

TABLE 43

Formulation in Example 29
Formulation 36

| Components | % Wet | % Dry |
|---|---|---|
| Water | 75.00 | — |
| Pullulan | 13.00 | 52.00 |
| Xanthan gum | 0.15 | 0.60 |
| Glycerin | 1.25 | 5.00 |
| Menthol | 1.25 | 5.00 |
| Sorbitol | 1.25 | 5.00 |
| Tween 80 | 1.00 | 4.00 |
| Span 80 | 0.50 | 2.00 |
| MCT oil | 3.60 | 14.40 |
| Montelukast Sodium (or freebase) | 3.00 | 12.00 |
| Total | 100.00 | |
| Total Dry Mass | 25.00 | 100.00 |

TABLE 44

Formulation in Example 30
Formulation 37

| Components | % Wet | % Dry |
|---|---|---|
| Water | 84.25 | — |
| PEG-35 Castor Oil | 2.11 | 13.37 |
| Sucralose | 1.05 | 6.68 |
| Menthol | 1.05 | 6.68 |
| Xanthan gum | 0.08 | 0.53 |
| locust bean gum | 0.08 | 0.53 |
| carrageenan | 0.84 | 5.35 |
| Pullulan | 8.42 | 53.48 |
| Montelukast Sodium (or freebase) | 2.11 | 13.37 |
| Total | 100.00 | |
| Total Dry Mass | 15.75 | 100.00 |

TABLE 45

Formulation in Example 31
Formulation 38

| Components | % Wet | % Dry |
|---|---|---|
| Water | 63.68 | — |
| Sucralose | 1.00 | 2.74 |
| Menthol | 1.00 | 2.74 |
| Tween 80 | 1.00 | 2.74 |
| HPC | 14.93 | 41.10 |
| MCC | 3.98 | 10.96 |

TABLE 45-continued

Formulation in Example 31
Formulation 38

| Components | % Wet | % Dry |
|---|---|---|
| MCT oil | 8.96 | 24.66 |
| PEG 400 | 1.00 | 2.74 |
| Montelukast Sodium (or freebase) | 4.48 | 12.33 |
| Total | 100.00 | |
| Total Dry Mass | 36.32 | 100.00 |

TABLE 46

Formulation in Example 32
Formulation 39

| Components | % Wet | % Dry |
|---|---|---|
| Water | 75.00 | — |
| Pullulan | 13.00 | 52.00 |
| Xanthan gum | 0.15 | 0.60 |
| Glycerin | 1.25 | 5.00 |
| Menthol | 1.25 | 5.00 |
| Sorbitol | 1.25 | 5.00 |
| Tween 80 | 1.00 | 4.00 |
| Span 80 | 0.50 | 2.00 |
| MCT oil | 3.60 | 14.40 |
| Zafirlukast | 3.00 | 12.00 |
| Total | 100.00 | |
| Total Dry Mass | 25.00 | 100.00 |

TABLE 47

Formulation in Example 33
Formulation 40

| Components | % Wet | % Dry |
|---|---|---|
| Water | 63.68 | — |
| Sucralose | 1.00 | 2.74 |
| Menthol | 1.00 | 2.74 |
| Tween 80 | 1.00 | 2.74 |
| HPC | 14.93 | 41.10 |
| MCC | 3.98 | 10.96 |
| MCT oil | 8.96 | 24.66 |
| PEG 400 | 1.00 | 2.74 |
| Zafirlukast | 4.48 | 12.33 |
| Total | 100.00 | |
| Total Dry Mass | 36.32 | 100.00 |

TABLE 48

Formulation in Example 34
Formulation 41

| Components | % Wet | % Dry |
|---|---|---|
| Water | 63.68 | — |
| Sucralose | 1.00 | 2.74 |
| Menthol | 1.00 | 2.74 |
| Tween 80 | 1.00 | 2.74 |
| HPC | 14.93 | 41.10 |
| MCC | 3.98 | 10.96 |
| MCT oil | 8.96 | 24.66 |

TABLE 48-continued

Formulation in Example 34
Formulation 41

| Components | % Wet | % Dry |
| --- | --- | --- |
| PEG 400 | 1.00 | 2.74 |
| Zafirlukast | 4.48 | 12.33 |
| Total | 100.00 | |
| Total Dry Mass | 36.32 | 100.00 |

TABLE 49

Formulation in Example 35
Formulation 42

| Component | % Wet | % Dry |
| --- | --- | --- |
| Water | 76.42 | — |
| Pullulan | 12.42 | 52.67 |
| Xanthan gum | 0.15 | 0.65 |
| glycerin | 1.24 | 5.27 |
| Sorbitol | 1.24 | 5.27 |
| Tween 80 | 2.48 | 10.53 |
| Sucralose | 0.96 | 0.50 |
| Peppermint oil | 0.25 | 1.05 |
| MCT oil | 2.48 | 10.53 |
| Synthetic THC | 2.35 | 9.97 |
| Total Mass | 100 | — |
| Total Dry Mass | — | 100 |

TABLE 50

Formulation in Example 36
Formulation 43

| Component | % Wet | % Dry |
| --- | --- | --- |
| Water | 76.78 | — |
| Glycerin | 1.53 | 6.60 |
| Sucralose | 0.92 | 3.94 |
| Ammonium Glycyrrhizate | 0.46 | 1.97 |
| Flavor herb oil | 0.24 | 1.03 |
| Tween 80 | 1.45 | 6.24 |
| Span 80 | 0.87 | 3.74 |
| Microcystalline cellulose | 3.6 | 12.16 |
| Hydroxy propyl cellulose | 9.8 | 45.6 |
| MCT oil | 2.61 | 11.23 |
| CBD oil | 1.74 | 7.49 |
| Total Mass | 100 | — |
| Total Dry Mass | — | 100 |

TABLE 51

Formulation in Example 37
Formulation 44

| Component | % Wet | % Dry |
| --- | --- | --- |
| Water | 76.39 | — |
| hydrogenated castor oil | 1.10 | 5.40 |
| Pectin | 6.20 | 26.13 |
| Guar gum | 0.80 | 3.33 |
| Sucralose | 0.80 | 3.33 |
| Hydroxylated Lecithin | 2.14 | 8.85 |

TABLE 51-continued

Formulation in Example 37
Formulation 44

| Component | % Wet | % Dry |
| --- | --- | --- |
| Sesame oil | 10.30 | 43.40 |
| Cannabis oil | 2.27 | 9.56 |
| Total Mass | 100 | — |
| Total Dry Mass | — | 100 |

According to some embodiment, the OF preferably disintegrate in the mouth or in vitro within 20 minutes, within 18 minutes, within 15 minutes, within 12 minutes, 10 min, within 8 minutes, within 6 minutes, within 5 minutes, within 4 minutes, within 3 minutes, within 2 minutes, within 1 minutes.

The OF according to embodiments of the present disclosure must be formed into a thin sheet prior to initiating the drying phase. After the desired components are combined to form a multi-component matrix, including the polymer, water, carrier oil, surfactant and a lipophilic active, and other components as desired, the combination is formed into a sheet or film, by any method known in the art such as, coating, spreading, casting or drawing the multi-component matrix. A multi-layered film may be achieved by coating, spreading, or casting a combination onto an already formed film layer. Although a variety of different film-forming techniques may be used, it is desirable to select a method that will provide a flexible OF, such as reverse roll coating. The flexibility of the OF allows for the thin sheets of OF to be rolled and transported for storage or prior to being cut into individual dosage forms. Desirably, the OF will also be self-supporting or in other words able to maintain their integrity and structure in the absence of a separate support. Furthermore, the films of the present invention may use selected materials that are edible or ingestible.

Coating or casting methods are particularly useful for the purpose of forming OF as disclosed herein. Specific examples include reverse roll coating, forward roll coating, gap or knife over roll coating, air knife coating, curtain coating, or combinations thereof, especially when a multi-layered film is desired.

Roll coating, or more specifically reverse roll coating, is particularly desired when forming films in accordance with the present disclosure. This procedure provides excellent control and uniformity of the resulting films, which is desired in the present disclosure. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

According to other embodiments, it may be desirable to have a multilayer OF designed with a first layer comprising a cannabinoid and a second layer having a different cannabinoid. Cannabinoids though similar have differing solubility and lipophilicity. Having a layer comprising a single cannabinoid of a combination of cannabinoids with similar lipophilicity and affinity to a particular oil is desirable for ease in scaling up the manufacturing of large scale OF production.

According to some embodiments, a disclosed OF comprises a first layer having a first cannabinoid and a first carrier oil, and a second layer having a second cannabinoid and a second carrier oil, where the first cannabinoid and the second cannabinoid is different from the first cannabinoid and where the first carrier oil is different than the second carrier oil. This multilayer film further comprises a first of surfactant in the first later and a second surfactant in the second layer. In some embodiment the quantity of the first and second surfactants are different later having a different cannabinoid. The multilayer approach of manufacturing OF is favored for its ease of manufacture having a targeted formulation for a specific lipophilicity. The optimized liquid formulations are made for 0.01%, 1%, 2%, 3%, 4%, 5%, 6%, 7%, 8%, 9%, 10%, 15%, 20%, 25%, 30% of a specific cannabinoid compound and in concentration of 0.01%, 1%, 2%, 3%, 4%, 5%, 6%, 7%, 8%, 9%, 10%, 15%, 20%, 25%, 30% of a different cannabinoid. This allowed the manufacture of any casting of a multilayer film having a first layer having 10% CBD and subsequently casting a second layer having 10% THC making a combined dosage of a bilayer film with combine dosing of 50/50 CBD/THC. This novel approach would allow for scaling and making a significant amount of different OF for the desired combination and thus meeting the consumer or patient population needs of various combination of therapeutic or recreational effects. The use of this modular approach also reduces cost of production by limiting the necessity of scale up formulation having the combined composition of cannabinoids. For instance, 30 separate blends with each having 0.01%, 1%, 2%, 3%, 4%, 5%, 6%, 7%, 8%, 9%, 10%, 15%, 20%, 25%, 30% of a specific cannabinoid compound and in concentration of 0.01%, 1%, 2%, 3%, 4%, 5%, 6%, 7%, 8%, 9%, 10%, 15%, 20%, 25%, 30% of a different cannabinoid while being able to have up to 225 different oral film dosage forms derived from those 30 blends. In addition, one could make a trilayer film with the third layer having an identical or different cannabinoid allowing for the manufacture of an even greater variation of safe and effective cannabinoid dosing. According to certain embodiments, the OFs have an acidic pH. OFs have a surface pH lower than 7, preferably lower than 5.5, more preferably lower than 4.

According to certain embodiments, the formulation is suitable for chewable/edible OFs. According to some embodiment, OCF formulations contain lipophilic actives and food grade inactive ingredients and comply with all properties of safe-food ingredients according to Food and Drug Administration (FDA) having Generally Recognized As Safe (GRAS) status. Additionally, the edible/chewable OFs or OCF have lower mucoadhesion properties and disintegrate smoothly in the mouth at a moderate rate either with or without actual chewing. OCFs have a smooth texture upon disintegration, are pleasant tasting and leave no bitter or unpleasant taste.

Polymers suitable for formulating OCFs include, but not limited to polypeptides (e.g., collagen and geltain), hydrocolloids (e.g., starch alginate, carrageenan, carboxymethyl-cellulose, gum arabic, chitosan, pectin, and xanthan gum), lipids (e.g., acetylated monoglycerides, natural wax, and surfactants). One of the limiting factor of making edible OF is the low variety of food grade surfactant. This highly complex constraint of making an edible OF without the variety of pharma grade surfactant makes it even more challenging.

According to some embodiment, the edible OF containing only food grade component formulations uses HPMC as an emulsion stabilizer.

The formulation in Example 8, 10, 13 and 14 are suitable for an edible/chewable OF.

The disclosed OF are well suited for many uses. The high degree of desired active uniformity in the OF makes them particularly well suited for incorporating cannabinoids and cannabinoid derivative. Furthermore, the polymers used in construction of the OF may be chosen to allow for a range of disintegration times for the OF. A variation or extension in the time over which a film will disintegrate may achieve control over the rate that the active is released, which may allow for a sustained release delivery system.

The OF are used to orally administer a lipophilic active. This is accomplished by preparing the films as described above and introducing them to the oral cavity of a human or animal, such as a mammal. This film may be prepared and adhered to a second or support layer from which it is removed prior to use, i.e. introduction to the oral cavity. An adhesive may be used to attach the OF to the support or backing material which may be any of those known in the art, and is preferably not water soluble. If an adhesive is used, it will desirably be a food-grade material that is ingestible and does not alter the properties of the active.

When designed for animal administration, the OF may desirably be designed to adhere to the oral cavity of the animal including the tongue, thus preventing it from being ejected from the oral cavity and permitting more of the active to be introduced to the oral cavity as the film disintegrates.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

The films of the present invention are desirably packaged in sealed, air and moisture resistant packages to protect the active from exposure oxidation, hydrolysis, volatilization and interaction with the environment. Moreover, the films of the present invention dissolve quickly upon contact with saliva or mucosal membrane areas, eliminating the need to wash the dose down with water.

Desirably, a series of such unit doses are packaged together in accordance with the prescribed regimen or treatment, e.g., a 3-90 day supply, depending on the particular therapy. The individual films can be packaged on a backing and peeled off for use.

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. An emulsion based oral film dosage form for human or animal administration comprising:
   a. an unbuffered oil in water emulsion based continuously cast film layer comprising:
      i. a carrier oil;
      ii. an amphiphilic pharmaceutical active; and
      iii. a water soluble film forming polymer;
   b. wherein the amphiphilic pharmaceutical active exhibits surfactant properties;
   c. wherein the combined quantity of carrier oil and amphiphilic pharmaceutical active is more than about 20% (wt/wt) of the oral film dosage form; and d. wherein the film layer has a contact angle of less than 90 degrees.

2. The oral film dosage form of claim 1, wherein the amphiphilic pharmaceutical active is Montelukast.

3. The oral film dosage form of claim 2, further comprising a chelating agent.

4. An oral film dosage form for human or animal administration comprising:
   a film layer comprising:
      a. a lipophilic active;
      b. a carrier oil;
      c. a water soluble film forming polymer;
   wherein the film layer has a surface pH equal or lower than 4 and
   wherein the film layer has a contact angle of less than 90 degrees.

5. The oral film dosage form of claim 4, wherein the combined quantity of carrier oil and lipophilic active is more than about 25% (wt/wt) of the oral film dosage form.

6. The oral film dosage form of claim 4, wherein the combined quantity of carrier oil and lipophilic active is more than about 40% (wt/wt) of the oral film dosage form.

7. The oral film dosage form of claim 4, wherein the film layer further comprises a viscosity modifier.

8. The oral film dosage form of claim 4, wherein the film layer retains at least 95% of the oil and lipophilic active.

9. The oral film dosage form of claim 4, wherein the contact angle of the film is below 80 degrees.

10. The oral film dosage form of claim 8, wherein the contact angle of the film is below 70 degrees.

11. The oral film dosage form of claim 4, wherein the contact angle of the film is below 60 degrees.

12. The oral film dosage form of claim 4, wherein the lipophilic active is THC and the carrier oil is MCT oil.

13. The oral film dosage form of claim 4, further comprising pectin in the film layer comprising the lipophilic active or in a one or more protective layers joined to the film layer comprising the lipophilic active, the pectin being present in an amount effective to provide targeted enteric delivery of the lipophilic active to the colon or large intestine upon administration.

14. An emulsion based edible oral film dosage form for human or animal administration comprising:
   a. a film layer comprising
      i. a lipophilic active;
      ii. a carrier oil; and
      iii. a water soluble film forming polymer;
   wherein all components are food grade; and
   wherein the film layer has a surface pH equal or lower than 4 and
   wherein the film layer has a contact angle of less than 90 degrees.

15. The emulsion based edible oral film dosage form of claim 14 wherein the polymer is HPMC.

16. The emulsion based edible oral film dosage form of claim 15 wherein the emulsion is stabilized by a polymer and where the oral film further comprises a cannabinoid.

17. The emulsion based edible oral film dosage form of claim 14 further comprising two protective layers, each of which is joined to one of opposite sides of the film layer, the protective layers each comprising a basifying agent or base buffering component that maintains a basic pH environment when the dosage form is orally administered.

18. The oral film dosage form of claim 17 wherein the combined quantity of carrier oil and lipophilic active is more than about 40% (wt/wt) of the oral film dosage form.

19. The oral film dosage form of claim 1, wherein the carrier oil is present in an amount of 10-40% w/w of the oral film dosage form.

20. The oral film dosage form of claim 4, wherein the carrier oil is present in an amount of 10-40% w/w of the oral film dosage form.

* * * * *